(12) United States Patent
Reynolds

(10) Patent No.: US 10,912,722 B2
(45) Date of Patent: Feb. 9, 2021

(54) STABILIZED STANNOUS COMPOSITIONS

(71) Applicant: THE UNIVERSITY OF MELBOURNE, Parkville (AU)

(72) Inventor: Eric Charles Reynolds, Parkville (AU)

(73) Assignee: THE UNIVERSITY OF MELBOURNE, Parkville (AU)

(*) Notice: Subject to any disclaimer, the term of this patent is extended or adjusted under 35 U.S.C. 154(b) by 46 days.

(21) Appl. No.: 15/105,748

(22) PCT Filed: Dec. 24, 2014

(86) PCT No.: PCT/AU2014/050447
§ 371 (c)(1),
(2) Date: Jun. 17, 2016

(87) PCT Pub. No.: WO2015/095932
PCT Pub. Date: Jul. 2, 2015

(65) Prior Publication Data
US 2016/0317404 A1    Nov. 3, 2016

(30) Foreign Application Priority Data

Dec. 24, 2013 (AU) .................... 2013905081
Apr. 3, 2014 (AU) .................... 2014901202
Sep. 24, 2014 (AU) .................... 2014903815

(51) Int. Cl.
| A61K 8/19 | (2006.01) |
| A61K 8/24 | (2006.01) |
| A61Q 11/00 | (2006.01) |
| A61K 33/42 | (2006.01) |
| A61K 33/24 | (2019.01) |
| A61K 9/00 | (2006.01) |
| A61K 9/68 | (2006.01) |
| A61K 6/20 | (2020.01) |
| A61K 6/74 | (2020.01) |

(52) U.S. Cl.
CPC .................. A61K 8/19 (2013.01); A61K 6/20 (2020.01); A61K 6/74 (2020.01); A61K 8/24 (2013.01); A61K 9/006 (2013.01); A61K 9/0056 (2013.01); A61K 9/0058 (2013.01); A61K 33/24 (2013.01); A61K 33/42 (2013.01); A61Q 11/00 (2013.01); *A61K 2800/52* (2013.01)

(58) Field of Classification Search
CPC ... A61K 6/74; A61K 8/24; A61K 6/20; A61K 33/24; A61K 9/006; A61K 8/19; A61K 9/0058; A61K 33/42; A61K 9/0056; A61K 2300/00; A61K 2800/52; A61P 1/02; A61Q 11/00
See application file for complete search history.

(56) References Cited

U.S. PATENT DOCUMENTS

| 3,864,471 A | 2/1975 | King et al. |
| 3,966,901 A | 6/1976 | Cullum et al. |
| 4,080,440 A | 3/1978 | DiGiulio et al. |
| 4,157,386 A | 6/1979 | La Rochelle |
| 4,357,318 A | 11/1982 | Shah et al. |
| 4,522,805 A | 6/1985 | Gordan |
| 4,588,763 A | 5/1986 | Brannstrom et al. |
| 4,672,032 A * | 6/1987 | Slavkin .................. C07K 14/47 424/49 |
| 5,015,628 A | 5/1991 | Reynolds et al. |
| 5,227,154 A * | 7/1993 | Reynolds ................. A61K 8/64 424/49 |
| 5,427,769 A | 6/1995 | Berrocal et al. |
| 5,520,725 A | 5/1996 | Kato et al. |
| 5,833,953 A | 11/1998 | Berrocal et al. |
| 5,981,475 A | 11/1999 | Reynolds |
| 6,036,944 A | 3/2000 | Winston et al. |
| 6,056,930 A | 5/2000 | Tung |
| 6,149,894 A | 11/2000 | Yamane et al. |
| 6,214,101 B1 | 4/2001 | Nakaseko |
| 6,652,875 B1 | 11/2003 | Bannister |

(Continued)

FOREIGN PATENT DOCUMENTS

| AU | 718253 | 7/1997 |
| EA | 011125 B1 | 12/2008 |

(Continued)

OTHER PUBLICATIONS

Fahad, et al., "Effect of casein phosphopeptide-amorphous calcium phosphate on the microhardness and microscopic features of the sound enamel and initial caries-like lesion of permanent teeth, compared to fluoridated agents," *Journal of Baghdad College Dentistry*, vol. 24, No. 4, pp. 114-120 (2012).

MI Paste™ and MI Paste Plus™ with RECALDENT™ (CPP-ACP) *Inside Dentistry*, Oct. 2012, vol. 8, No. 10 [online], [retrieved on Oct. 21, 2014]. Retrieved from internet , URL: www.dentalaegis.com/id/201 2/ 1O/mi-paste-and-mi-paste-p lus-with-recaldent-cpp-acp>, 6 pages.

(Continued)

Primary Examiner — Lezah Roberts
(74) Attorney, Agent, or Firm — Foley & Lardner LLP

(57) ABSTRACT

The present invention relates to improved complexes of amorphous calcium phosphate and/or amorphous calcium fluoride phosphate stabilised by phosphopeptides/phosphoproteins by addition of stannous ions. These complexes have anticariogenic properties useful to protect tooth structures as they remineralize (repair) early stages of dental caries and have other dental/medical applications (including anti-calculus, anti-erosion/corrosion and anti-dentinal hypersensitivity). Methods of making the complexes of the invention and of treatment or prevention of various dental conditions including dental caries, dental calculus, dental erosion/corrosion and dental hypersensitivity are also provided.

20 Claims, 7 Drawing Sheets

Specification includes a Sequence Listing.

(56) References Cited

U.S. PATENT DOCUMENTS

| | | | |
|---|---|---|---|
| 6,780,844 | B1 | 8/2004 | Reynolds |
| 7,312,193 | B2 | 12/2007 | Reynolds et al. |
| 7,491,694 | B2 | 2/2009 | Reynolds et al. |
| 8,603,988 | B2 | 12/2013 | Reynolds |
| 9,668,945 | B2 | 6/2017 | Reynolds |
| 10,695,370 | B2 | 6/2020 | Reynolds |
| 2002/0028251 | A1 | 3/2002 | Okay |
| 2002/0071858 | A1 | 6/2002 | Luo et al. |
| 2003/0124066 | A1 | 7/2003 | Dixon et al. |
| 2003/0152525 | A1* | 8/2003 | Dixon, Jr. ............... A61K 8/21 424/50 |
| 2003/0165442 | A1 | 9/2003 | Baig et al. |
| 2005/0063922 | A1 | 3/2005 | Reynolds et al. |
| 2005/0089481 | A1 | 4/2005 | Yamanaka et al. |
| 2005/0100581 | A1 | 5/2005 | Laurencin et al. |
| 2005/0118115 | A1 | 6/2005 | Fontenot |
| 2006/0183081 | A1 | 8/2006 | Bevilacqua et al. |
| 2007/0071858 | A1 | 3/2007 | Succar et al. |
| 2007/0254260 | A1 | 11/2007 | Alden et al. |
| 2008/0075675 | A1 | 3/2008 | Reynolds |
| 2008/0171001 | A1 | 7/2008 | Engelman et al. |
| 2008/0193557 | A1 | 8/2008 | Reynolds |
| 2009/0016972 | A1 | 1/2009 | Manasherov et al. |
| 2009/0022672 | A1 | 1/2009 | Reynolds |
| 2009/0324662 | A1 | 12/2009 | Kutsch et al. |
| 2010/0028273 | A1 | 2/2010 | Fischer et al. |
| 2011/0076241 | A1 | 3/2011 | Kato et al. |
| 2012/0129135 | A1 | 5/2012 | Yang et al. |
| 2013/0129641 | A1 | 5/2013 | Sadeghpour et al. |
| 2016/0158283 | A1 | 6/2016 | Reynolds |
| 2016/0317404 | A1 | 11/2016 | Reynolds |
| 2017/0333296 | A1 | 11/2017 | Reynolds |
| 2018/0008518 | A1 | 1/2018 | Reynolds |
| 2020/0197486 | A1 | 6/2020 | Reynolds |
| 2020/0246378 | A1 | 8/2020 | Reynolds |

FOREIGN PATENT DOCUMENTS

| | | | |
|---|---|---|---|
| EP | 0 786 245 A1 | | 7/1997 |
| EP | 1 525 878 A1 | | 4/2005 |
| EP | 1 952 801 A1 | | 8/2008 |
| EP | 2 301 513 A2 | | 3/2011 |
| EP | 2 353 576 A1 | | 8/2011 |
| JP | H08-026925 A | | 1/1996 |
| JP | 8-143436 A | | 6/1996 |
| JP | 10-290682 A | | 11/1998 |
| JP | 11-228327 | | 8/1999 |
| JP | 11-310599 A | | 11/1999 |
| JP | 3742523 | | 11/1999 |
| JP | 2001-144695 | | 11/2002 |
| JP | 2004-215521 A | | 8/2004 |
| JP | 2005-112841 | | 4/2005 |
| JP | 2005-145952 A | | 6/2005 |
| JP | 2010-047494 A | | 3/2010 |
| JP | 2013-163656 A | | 8/2013 |
| WO | WO 1982/003008 | | 9/1982 |
| WO | WO 1987/007615 | | 12/1987 |
| WO | WO 1993/003707 | | 3/1993 |
| WO | WO 1994/000146 A1 | | 6/1994 |
| WO | WO 1996/029340 | | 9/1996 |
| WO | WO 1997/036943 | | 10/1997 |
| WO | WO 1997/040811 | | 11/1997 |
| WO | WO 1998/040406 | | 9/1998 |
| WO | WO 2000/006108 | | 2/2000 |
| WO | WO 2000/057892 | | 10/2000 |
| WO | WO 2001/044106 A1 | | 6/2001 |
| WO | WO-02/094204 A1 | | 11/2002 |
| WO | WO 2003/059303 A2 | | 7/2003 |
| WO | WO 2003/059304 A1 | | 7/2003 |
| WO | WO 2004/035077 A1 | | 4/2004 |
| WO | WO 2004/054531 A1 | | 7/2004 |
| WO | WO-2004/060336 | | 7/2004 |
| WO | WO-2006/056013 A1 | | 6/2006 |
| WO | WO-2006/130913 | | 12/2006 |
| WO | WO-2006/135982 A1 | | 12/2006 |
| WO | WO-2007-090242 | | 8/2007 |
| WO | WO-2009/130447 A1 | | 10/2009 |
| WO | WO-2010-134904 | | 11/2010 |
| WO | WO-2013/117913 | | 8/2013 |
| WO | WO-2016/101041 A1 | | 6/2016 |
| WO | WO-2018/165707 A1 | | 9/2018 |

OTHER PUBLICATIONS

MI Paste™ and MI Paste Plus™ [retrieved on Oct. 21, 2014] Retrieved from internet ,URL: http://web.archive.org/web/20131223044 I 14/http://www.gcamerica.com/products/preventive/MI _ Paste/> published on Dec. 23, 2013 as per Wayback Machine whole document Wayback machine used to determine publication date, 2 pages.

MI Paste™ and MI Paste Plus™ [retrieved on Feb. 16, 2015] Retrieved from internet ,URL: http://web.archive.org/web/20140701070616/http://www.mipaste.com/about.php> published on Dec. 4, 2013 as per Wayback Machine whole document Wayback machine used to determine publication date, 2 pages.

Comar et al., "Effect of NaF, SnF2, andTiF4 Toothpastes on Bovine Enamel and Dentin Erosion-Abrasion In Vitro," *International Journal of Dentistry*, vol. 2012, Article IDS 134350, pp. 1-6 (Oct. 2012).

Baig, et al., "HAP Dissolution Study II: SnF2 vs. NaF Dentifrice Study". 87th Session of the IADR (International & American Associations for Dental Research) Apr. 1-4, 2009 [online], [retrieved on Oct. 21, 2014]. Retrieved from internet ,URL: dentalcare.com/media/en- US/research_ db/pdf/, p. 24.

Gisselsson, H., et al., "Effect of professional flossing with NaF or SnF2 gel on approximal caries in 13-16-year-old schoolchildren". Acta Odontologica Scandinavica, vol. 57, No. 2, pp. 121-125 (Jan. 1999).

Mintel, "Mineralising Toothpaste," from Database GNPD, database accession No. 1368327 (Aug. 2010).

Zero, "Dentifrices, mouthwashes, and remineralization/caries arrestment strategies," BMC Oral Health (Jul. 2006), 6(Suppl I):S9, pp. 1-13.

Farooq et al., "A review of novel dental caries preventative material: Casein phosphopeptide-amorphous calcium phosphate (CPP-ACP) complex," King Saud University Journal of Dental Sciences (2013) 4, 47-51.

U.S. Appl. No. 16/852,983, filed Apr. 20, 2020, Eric Charles Reynolds.

U.S. Appl. No. 16/492,903, filed Sep. 18, 2019, Eric Charles Reynolds.

Denes et al., "Oxidation of $SnF_2$ stannous fluoride in aqueous solutions," Hyperfine Interact 90: 435-439 (1994).

Sim et al., "Anti-caries effect of CPP-ACP in irradiated nasopharyngeal carcinoma patients," Clinical Oral Investigations vol. 19, No. 5, pp. 1005-1011 (2015).

International Search Report dated Sep. 15, 2014 in application No. PCT/AU2014/050144.

Supplementary European Search Report dated Dec. 13, 2016 in application No. EP 14 83 0019.

Adamson, et al., "The Analysis of Multiple Phosphoseryl-containing Casein Peptides using Capillary Zone Electrophoresis," *J. of Chromatography*, 646, pp. 391-396 (Jun. 1993).

Adamson et al., "Characteriztion of Tryptic Casein Phosphopeptides Prepared Under Industrially Relevant Conditions", Biotec. Bioeng., 45, pp. 196-204 (Feb. 1995).

Adamson et al., "High Performance Capillary Electrophoresis of Casein Phosphopeptides Containing 2-5 Phosphoseryl Residues; Relationship Between Absolute Electrophoretic Mobility and Peptide Charge and Size", Electrophoresis 16: pp. 525-528 (1995).

Adamson, et al., "Characterization of Casein Phosphopeptides Prepared Using Alcalase: Determination of Enzyme Specificity," *Enzyme and Microbial Tech.*, 19, pp. 202-207 (Aug. 1996).

Adebayo, O.A. et al. "Effects of conditioners on microshear bond strength to enamel after carbamide peroxide bleaching and/or casein phosphopeptide-amorphous calcium phosphate (CPP-ACP) treatment", Journal of Dentistry, vol. 35, 2007, pp. 862-870 (Aug. 2007).

Allais, G. "Karies—Die Therapie, Continuing Dental Education", pp. 716-735 (Jun. 2007), English Abstract provided.

(56) References Cited

OTHER PUBLICATIONS

Al-Zraikat, H. et al. "Incorporation of casein-phosphopeptide-amorphous calcium phosphate into glass ionomer cement." Abstract 0654—84th General Session of the IADR, Jun. 28-Jul. 1, 2006, Brisbane, Australia.
Al-Zraikat, H. et al. "Development of GIC incorporating Caesin Phosphopetide amorphous phosphate (CPP ACP) complex.", Australian Dental Journal ADRF Special Research Supplement, vol. 52, p. S4., (2007).
Angmar et al., "Studies on the Ultrastructure of Dental Enamel; J. Ultrastructure Research," 8, pp. 12-23 (1963).
Aoba et al. "Dental Fluorosis: Chemistry and Biology."Crit. Rev Oral Biol. Med. 13 (2) pp. 155-170 (2002).
Ardu et al., "A minimally invasive treatment of severe dental fluorosis"; Quintessence International; 38(6), pp. 455-458 (Jun. 2007).
Ardu, S. et al. "Minimally invasive treatment of white spot enamel lesions.", Quintessenz International, vol. 38, No. 8, pp. 633-636 (Sep. 2007).
Aytepe, Z. et al. "Effect of CCP-ACP on oral health of cerebral palsy children.", Abstract 3343, Jul. 2008, International Association for Dental Research, Toronto, Canada.
Bavetta et al., "Protein Factors and Experimental Rat Caries", Nutr. 63: pp. 107-117 (1957).
Benzian et al., "Total and free available fluoride in toothpastes in Brunei, Cambodia, Laos, the Netherlands and Suriname"; International Dental Journal, 62, pp. 213-221 (2012).
Biesbrock, A.R. et al. "Reversal of Incipient and Radiographic Caries Through The Use of Sodium and Stannous Fluoride Dentifrices in a Clinical Trial." The Journal of Clinical Dentistry vol. IX, No. 1, pp. 5-10 (Feb. 1998).
Biesbrock, Aaron R. "Relative anti-caries efficacy of 1100, 1700, 2200, and 2800 ppm fluoride ion in a sodium fluoride dentifrice over 1 year." Community Dentistry and Oral Epidemiology; 29, pp. 382-389 (Jan. 2001).
Biesbrock, Aaron R. et al. "Dose response efficacy of sodium fluoride dentrifice at 9 and 21 months with supervised brushing." American Journal of Dentistry, vol. 16, No. 5, (Oct. 2003).
Black et al. "Mottled Teeth" The Dental Cosmos. vol. LVIII. No. 2., pp. 129-156 (Feb. 1916).
Burwell, A.K. et al. "Quantitative Tubule Occlusion in an In Vitro Remineralization/Demineralization Model.", Abstract 0568, EADR 2006, Dublin, Ireland (Sep. 2006).
Burwell, A.K. et al. "Dentifrice Protection Against Dentin Demineralization in an In Vitro Study.", Abstract 1764, IADR, New Orleans, USA (Mar. 2007).
Cai et al., "Remineralization of Enamel Subsurface Lesions in Situ by Sugar-Free Lozenges Containing Casein Phosphopeptide-Amorphous Calcium Phosphate", Aus. Dent. J., 48: 4, pp. 240-243 (2003).
Cai, F. et al. "Remineralization by chewing gum containing CPP-ACP and citric acid." Abstract 190—84th General Session of the IADR, Brisbane, Australia, pp. 240-243 (Jun. 28, 2006-Jul. 1, 2006).
Cai, F. et al. "Effect of Addition of Citric Acid and Casein Phosphopeptide-Amorphous Calcium Phosphate to a Sugar-free chewing gum on Enamel Remineralization in Situ.", Caries Research, vol. 41, pp. 377-383 (Feb. 2007).
CAPLUS Copyright 2005. "NMR studies of a novel Calcium, phosphate and fluoride delivery vehicle <SYM97> S1-casein( 59-79) by stabilized amorphous calcium fluoride phosphate nanocomplexes.".
Carrillo, Dr. J et al. "Nuevos avances tecnológicos en Odontologia Conservadora", La Gaceta Dental, 193:213, pp. 218-219 (Jun. 2008), English Abstract.
Chalmers, J.M. "Minimal intervention dentistry: part I. Strategies for addressing the new caries challenge in older patients." JCDA, 72(5), pp. 427-433 (Jun. 2006).
Chalmers, J. et al. "Minimal Intervention Dentistry in the New Millennium.", DDS, MS. Dentaltown, pp. 54 (Feb. 2008).
Chelariu, C. et al. "Nuove prospettiva nella prevenzione della carie Congresso Nazionale del Collegio dei Docenti di Odontoiatria Roma", Apr. 5-7, 2006, Poster session, published by "Doctor Os", No. 3, Mar. 2006. English Abstract.
Chen, L. et al. "Calcium Release and Mechanical Properties of Experimental Calcium-Releasing Composites.", Abstract 2572, IADR, New Orleans, USA (Mar. 2007).
Cipolla, M. et al. "Fluoride and Calcium-Phosphate Effects on Fracture Toughness of Bleached Dentin.", Abstract 1032, Toronto, Canada (Jul. 2008).
Coates, L. "Tooth mousse shows some unexpected beneficial side effects." Dental Asia (Nov./Dec. 2004).
Cochrane, N.J. et al. "QLF and TMR analysis of CPP-ACFP remineralized enamel in vitro.", Abstract 192—84th General Session of the IADR, Brisbane, Australia (Jun. 28, 2006-Jul. 1, 2006).
Crisp, S., "Glass Ionomer Cement: Chemistry of Erosion", J. Dent. Res. 55: 1032-1041 (Apr. 1976).
Cross et al., "Cation-Dependent Structural Features of Beta-Casein-(1-25)", Biochem. J. (May 15, 2001), 356: Pt 1, pp. 277-286.
Cross, KJ et al. "Structural Characterization of Beta-casein(1-25)-ACFP Complex.", Aust Dent J ADRF Special Research Supplement, vol. 52, No. 4, S12, (2007).
Cross, K.J. et al. Structure and $^{15}$N-Dynamics of casein phosphopeptide-amorphous calcium phosphate nanocomplexes. Abstract 2534—84th General Session of the IADR, Jun. 28-Jul. 1, 2006, Brisbane, Australia.
Cross, et al. "Physicochemical Characterization of Casein Phosphopeptide-Amorphous Calcium Phosphate Nanocomplexes." The Journal of Biological Chemistry, vol. 280, No. 16. 15362-15369 (Apr. 2005).
Cross, KJ et al. "Structural Characterization of anticariogenic casein Phosphopeptide alphas2 casein(46-70) complexed with amorphous calcium phosphate.", Aust Dent J ADRF Special Research Supplement 52(4):S10-S11 (2007).
Cross, KJ et al. "Casein Phosphopeptides in Oral Health—Chemistry and Clinical Applications", Current Pharmaceutical Design, vol. 13, pp. 793-800 (2007).
Cross et al., "NMR Studies of a Novel Calcium, Phosphate and Fluoride Delivery Vehicle—The Multiphosphorylated Peptide Alpha S1-Casein (59-79) Complexed with Amorphous Calcium Fluoride Phosphate", Biomaterials., vol. 25, pp. 5061-5069 (Jan. 2004).
Cross et al. "Casein Phosphopeptide-Amorphous Calcium Phosphate Nanocomplexes: A Model of the Casini Micelle Core," Centre for Oral Health Science, School of Dental Science, The University of Melbourne, pp. 1-42, (Aug. 2008).
Cross et al., "Structural Studies of the b-Casein Phosphopeptide Bound to Amorphous Calcium Phosphate", IADR, General Session, Chiba, Abstract 0490, (2001).
Cross et al., "Ultrastructural Studies of the Casein Phosphopeptide-Amorphous Calcium Phosphate Nanoclusters", IADR, General Session, Chiba, Abstract 0491, (2001).
Curnow, M.M.T., et al. "A Randomised Controlled Trial of the Efficacy of Supervised Toothbrushing in High-Caries-Risk Children."Carie Research; 36:294-300 (Mar. 2002).
Database WPI Week 200316, Thomason Scientific, London, GB; 2003-165149, XP002537968 & SE 0 100 558 A, Mediteam Dental AB, Aug. 21, 2002, Abstract.
Davies, G.M., "A randomized controlled trial of the effectiveness of providing free fluoride toothpaste from the age of 12 months on reducing caries in 5-6 year old children." Community Dental Health 19, 131-136 (2002).
Deangelis et al., "Molecular modelling of anticariogenic Casein Phosphopeptide AS2-CN (2-20) NMR Spectroscopy Derived Constraints", Abstract 2997—82nd General Session of the IADR, Mar. 2004, Honolulu, Hawaii.
Denbesten, P.K. et al. "Biological Mechanisms of Fluorosis and Level and Timing of Systemic Exposure to Fluoride with Respect to Fluorosis." J. Dent Re 71(5): pp. 1238-1243 (May 1992).
Donovan, T. "Protocol for the prevention and management of root caries.", Journal Compilation, vol. 20, No. 6, pp. 405-411 (2008).
Duckworth, R.M. "Oral Fluoride Measurements for Estimation of the Anti-caries Efficacy of Fluoride Treatments." J Dent Res., pp. 836-840 (Apr. 1992).

(56) References Cited

OTHER PUBLICATIONS

Duckworth, R.M. "Effects of Mouthwashes of Variable NaF Concentration but Constant NaF Content on Oral Fluoride Retention." Caries Research 1994; 18, pp. 43-47 (1994).
Featherstone, Job et al. "An in situ model for simultaneous assessment of inhibition of demineralization and enhancement of Remineralization." J Dent Res vol. 71 (Spec. Iss.), pp. 804-810 (Apr. 1992).
Feinmann, J. "This won't hurt a bit.", The Times, Saturday, 2 pages, Mar. 12, 2005.
Fejerskov et al. "Dental fluorosis—a handbook for health workers." Munksgaard, Copenhagen, pp. 32-77 (copyright 1988).
Fejerskov et al. "The Nature of Mechanisms of Dental Fluorosis in Man." J Dent Res 69 (Spec Iss) pp. 692-700 (Feb. 1990).
Fejerskov et al. "Posteruptive changes in human dental fluorosis—a histological and ultrastructural study." Pro Finn Dent Soc vol. 87, No. 4, pp. 607-619 (1991).
Fejerskov et al. "Fluoride in Dentistry 2nd edition." Munksgaard, Copenhagen, pp. 112-152 (Copyright 1996).
Ferrazzano, G.F. et al. "Nuove strategie nella prevenzione della carie dentaria:studio sperimentale sui caseinofosfopeptidi." Prevenzione Odontostomatologica vol. 4, 2005, pp. 15-21. English Abstract.
Ferrazzano, G.F. et al. "New Strategies in dental caries prevention: experimental study on casein phosphopetide.", European Journal of Paedetric Dentistry, 4, pp. 183-187 (Apr. 2007).
Ferrazzano, G. et al. "Protective effect of yogurt extract on dental enamel demineralization in vitro.", Australian Dental Journal, vol. 53, pp. 314-319 (Feb. 2008).
Freml, L. et al. "Efficacy of Hypersensitivity Agents on Demineralization under Provisional Crowns." Abstract 1346, IADR Mar. 2007, New Orleans, USA.
Fuller, B.L. et al. "Efficacy of MI Paste in Preventing Demineralization in Overdenture Abutments.", Abstract 0503, IADR Mar. 2007, New Orleans, USA.
Gagnaire et al., "Phosphopeptides interacting with colloidal calcium phosphate isolated by tryptic hydrolysis of bovine casein micelles", Journal of Dairy Research (Feb. 1996), 63, pp. 405-422.
Gandolfi, M. et al. "Calcium silicate coating derived from Portland cement as treatment for hypersensitive dentine", Journal of Dentistry, vol. 36, 2008, pp. 565-578.
Giambro, N.J. et al. "Characterization of Fluorosed Human Enamel by Color Reflectance, Ultrastructure, and Elemental Composition." Caries Res. Issue 29 (Jan. 1995) pp. 251-257.
Giniger et al. "A 180-Day Clinical Investigation of the Tooth Whitening Efficacy of a bleaching Gel with Added Amorphous Calcium Phosphate." J. of Clinical Dentistry. vol. XVI. No. 1. 2005. pp. 11-16.
Giniger et al. "The clinical performance of professionally dispensed bleaching gel with added amorphous calcium phosphate." JADA. vol. 136. Mar. 2005. pp. 383-392.
Gugnani, S. et al. "Comparative evaluation of two commercially available desensitising agents after scaling and root planning: an in vivo study", PERIO, vol. 5, No. 2, 2008, pp. 121-129.
Haderlie, D.D. et al. "MI Paste and Fluoride effects on Secondary Caries.", Abstract 0504, IADR Mar. 2007, New Orleans, USA.
Harper et al., "Cariostatic Evaluation of Cheeses with Diverse Physical and Compositional Characteristics", Caries Res. 20: pp. 123-130 (1986).
Harper et al., "Modification of Food Cariogenicity in Rats by Mineral-Rich Concentrates from Milk", J. Dent Res. 66: pp. 42-45 (Jan. 1987).
Hartshone, JE. "The relationship between plaque index scores, fluoride content of plaque, plaque pH, dental caries experience and fluoride concentration in drinking water in a group of primary school children." Journal of the Dental Association of South Africa, 49, pp. 5-10, Jan. 1994.
Hay et al., "A Clinical Trial of the Anticaries Efficacy of Casein Derivatives Complexed with Calcium Phosphate in Patients with Salivary Gland Dysfunction", Oral. Surg. Oral Med Oral. Pathol Oral Radiol. Endod. (Mar. 2002); 93: pp. 271-5, 2002.
Hicks, J. et al. "Biological factors in dental caries: role of remineralization and fluoride in the dynamic process of demineralization and remineralization (part 3)." The Journal of Clinical Pediatric Dentistry. vol. 28, No. 3, pp. 203-214 (2004).
Hicks, J. et al. "Casein Phosphopeptide-Amorphous calcium phosphate paste: root surface caries formation.", Abstract 3275—IADR, Mar. 2005, Baltimore, Maryland, USA, Abstract.
Hidaka, et al., "A New Method for Study of the Formation and Transformation of Calcium Phosphate Precipitates: Effects of Several Chemical Agents and Chinese Folk Medicines," *Archives of Oral Biol.*, 36:1, pp. 49-54 (1991).
Holler, B. E. et al. "Fluoride uptake and distribution in enamel and dentin after application of different fluoride solutions." Clin Oral Invest, vol. 6, 2002, pp. 137-144.
Holloway et al., "Effects of Various Sucrose-Casein Ratios in Purified Diets on the Teeth and Supporting Structures of Rats", Arch Oral Bioi. 3: pp. 185-200 (1961).
Holt, et al., "Ability of a b-casein Phosphopeptide to Modulate the Precipitation of Calcium Phosphate by Forming Amorphous Dicalcium Phosphate Nanoclusters," *Biochem J.*, 314, 1035-1039 (1996).
Holt, Carl. "An equilibrium thermodynamic model of the sequestration of calcium phosphate by casein micelles and its application to the calculation of the partition of salts in milk." European Biophysics Journal. (Jan. 2004) pp. 421-434.
Huang, A. et al. "Remineralization of eroded teeth using CPP-ACP paste.", Abstract 3267, Jul. 2008, International Association for Dental Research, Toronto, Canada.
Huq, et al., A H-NMR Study of the Casein Phosphopeptide $a_{s1}$ Casein (59-79) *Biochimica et Biophysica Acta*, 1247, 201-208 (1995).
Huq et al., "Molecular Modeling of the Multiphosphorylated Sequence Motif Bound to Hydroxyapatite Surfaces" (59-79), J. Mol. Mode (Feb. 2000), 6:35-47.
Huq, et al. "Nascent Helix in the Multiphosphorylated Peptide $a_{s2}$—Casein(2-20)." Journal of Peptide Science, (2003) pp. 386-392.
Huq et al., "Molecular Modelling of the Multiphosphorylated Casein Phosphopeptide Alpha S1-Casein (59-79) based on NMR constraints," J. Dairy Res. 71:28-32 (2004).
Iijima et al., "Acid Resistance of Enamel Subsurface Lesions Remineralized by a Sugar-Free Chewing Gum Containing Casein Phosphopeptide-Amorphous Calcium Phosphate (CPP-ACP)", Caries, Res. Jan. 2004; 38: pp. 551-556.
Iijima, Y. et al. "Acid resistance of remineralized enamel by a sugar-free chewing gum.", Abstract 184—84th General Session of the IADR, Jun. 28-Jul. 1, 2006, Brisbane, Australia.
Inaba, D et al. "Effect of Sodium Hypochlorite Treatment on Remineralization of Human Root Dentine in vitro." Caries Research 1996, vol. 30 pp. 218-224.
Inaba, D. et al. "Intraoral changes in NaOCl-treated Root Dentin Lesions: A Pilot Study.", J. Dental Health, vol. 50, Jul. 2000, pp. 824-826. Abstract.
International Search Report for related PCT/AU2006/000885 dated Sep. 25, 2006.
Japanese Examination Report for corresponding Japanese Patent Application No. 2008-515000 dated Mar. 7, 2013. English Translation.
Kandelman, D et al. "A 24-month clinical study of the incidence and progression of dental caries in relation to consumption of chewing gum containing xylitol in school preventive programs." J Dent Res vol. 69(11), Nov. 1990, pp. 1771-1775.
Kariya et al., "Fluoride Effect on Acid Resistance Capacity of CPP-ACP Containing Material", Abstract 2045—82nd General Session of the IADR, (Mar. 2004), Honolulu, Hawaii. Abstract.
Kariya, S. et al. "Remineralization of enamel lesion by a novel cream with both CPP-ACP and fluoride.", Poster session 136—54th Annual ORCA Congress, 2007. Abstract.
Keçik, D. et al. "Effect of Acidulated Phosphate Fluoride and Casein Phosphopeptide-Amorphous Calcium Phosphate Application on Shear Bond Strength of Orthodontic Brackets." Angle Orthodontist, vol. 78, No. 1, 2008, pp. 129-133.
Khan, Dr. S. "White Spots on Teeth", Buzzle.com Intelligent Life on the Web, Jan. 2010.

(56) References Cited

OTHER PUBLICATIONS

Kim, K. et al. "Remineralization of the artificial caries lesion using CPP-ACP and fluoride.", Abstract 3280, Jul. 2008, International Association for Dental Research, Toronto, Canada.

Kowalczyk et al. "Evaluation of the product based on Recaldent™ technology in the treatment of dentin hypersensitivity.", Advances in Medical Sciences, vol. 51 suppl 1, 40-42, Mar. 2006.

Krobicka et al., "The Effects of Cheese Snacks on Caries in Desalivated Rats", J. Dent Res. 66:1116-19, (Jan. 1987).

Kumar, VLN et al. "The effect of casein phosphopeptide-amorphous calcium phosphate on remineralization of artificial caries-like lesions: an in vitro study.", Australian Dental Journal, vol. 53, 2008, pp. 34-40.

Larsson, K. S., et al. "Fluoride concentration in plaque in adolescents after topical application of different fluoride varnishes." Clin Oral Invest. (2000) 4:31-34.

Lasfargues, J. et al. "La remineralisation des lesions carieuses (2) synergies therapautiques Realites Cliniques.", vol. 15, No. 3, 2004 pp. 261-275. English Abstract.

Legeros, RZ "Calcium phosphates in demineralization/remineralization processes." J Clinical Dent X, 1999, pp. 65-73.

Lewis, J. "Brush, floss and mousse?" Women Dentistry Journal, Winter 2005, vol. 2, Issue 4, 18-19.

Little, Elaine et al. "An equilibrium thermodynamic model of the sequestration of calcium phosphate by casein phosphopeptides." European Biophysics Journal. (Jan. 2004) 33, 435-447.

Loesche, WJ "Role of *Streptococcus mutans* in human dental decay." Microbial. Rev. vol. 50(4), Dec. 1950, pp. 353-380.

Lynch, R.J.M. et al, "Low-Levels of Fluoride in plaque and saliva and their effect on the demineralization and remineralisation of enamel; role of fluoride of toothpastes." International Dental Journal (2004) vol. 54/ No. 5, 304-309.

Malcmacher, L. "Vitamins for teeth.", Common Sense Dentistry, Dental economics Oct. 2006, 130 and 144.

Malcmacher, L. "Enamel Remineralization: The Medical Model of Practicing Dentistry.", Dentistry Today, Nov. 2006, 4 pages.

Manton, D.J. et al. "In situ remineralisation by sugar-free gums, one containing CPP-ACP." Abstract 0020—45th Annual Meeting of Australian/New Zealand Division of the IADR, Sep. 2005, pp. 25-28.

Manton, D.J. "Promoting remineralization: using casein phosphopeptide-stabilized amorphous calcium (fluoride) phosphate. A chemical approach." EAPD, Amsterdam 8-II Jun. 2006, Abstract.

Manton, D.J. et al. "Remineralization of white spot lesions in situ by tooth mousse." Abstract 185—84th General Session of the IADR, Jun. 28-Jul. 1, 2006, Brisbane, Australia, Abstract.

Manton, D. "Dental Caries: Where to From Here?", Ann Roy Austral Coll Dent Surg, vol. 19, 2008, pp. 73-76.

Manton, D. et al. "Effect of ozone and Tooth Mousse™ on the efficacy of peroxide bleaching.", Australian Dental Journal, vol. 53, 2008, pp. 128-132.

Manton, D. et al. "Remineralization of enamel subsurface lesions in situ by the use of three commercially available sugar-free gums.", International Journal of Paediatric Dentistry, vol. 18, 2008, pp. 284-290.

Mazzaoui et al.,"Incorporation of Casein Phosphopeptide-Amorphous Calcium Phosphate into a Glass-ionomer Cement," J Dent Res 82(11): 914-918, Jul. 2003.

Mazzaoui, S.A. et al. "Incorporation of Casein Phosphopeptide-Amorphous Calcium Phosphate into a Glassionomer Cement." School of Dental Science, The University of Melbourne Research Reports (Jul. 2003) pp. 914-918.

Melkers, M.J. "Keeping focused on the finish line. Accomplishing goals with traditional and progressive technologies.", Dentaltown, vol. 5—Issue 11, Nov. 2004, pp. 60, 62, 64 & 66.

Mickenautsch, S. "An Introduction to Minimal Intervention Dentistry (MI).", Dental News, vol. XIV, No. IV, 2007, pp. 13-20.

Milnar, F.J. "Considering biomodification and remineralization techniques as adjuncts to vital tooth-bleaching regimens.", Compendium vol. 28, No. 5, May 2007, pp. 234-240.

Minami et al., "Effects of Cheese and Milk Containing CPP-ACP on Enamel Remineralization", 2049—82nd General Session of the IADR, Mar. 2004, Honolulu, Hawaii. Abstract only.

Minimum Intervention: modernes Kariesmanagement—Weg vom chirurgichen, hin zum medizinischen Versorgungsansatz mit GC. IDS—31st International Dental Show, Cologne, Apr. 12-16, 2005 (Today—Independent Trade Show Daily—Saturday) English Abstract.

Misra, S. et al. "Early Childhood Caries—A Review.", Dental Update, vol. 34, Dec. 2007, pp. 556-564. Abstract.

Miyazaki, M. et al. "Using ultrasound transmission velocity to analyze demineralization of tooth substrate." Abstract 94—52nd ORCA Congress, Jul. 2005, Indianapolis, USA | Caries Res vol. 39:319.

Morgan, M. V. et al. CPP-ACP gum slows progression and enhances regression of dental caries. Abstract 2445—84th General Session of the IADR, Jun. 28-Jul. 1, 2006, Brisbane, Australia. Abstract.

Morgan, MV et al. "A Clinical Trial Measuring White Spot Lesion Progression and Regression.", Abstract 0112, Jul. 2008, Toronto, Canada.

Morgan, MV et al. "Clinical trial of tooth mousse on white spot lesions.", Cooperative research Centre for oral health science. Toronto, Briefing paper No. 2, 2008.

Morgan, MV et al. "The Anticariogenic Effect of Sugar-Free Gum Containing CPP-ACP Nanocomplexes on Approximal Caries Determined Using Digital Bitewing Radiography.", Caries Research, vol. 42, pp. 171-184, 2008.

Moule, C.A. et al. "Resin bonding using an all-etch or self-etch adhesive to enamel after carbamide peroxide and/or CPP-ACP treatment.", Australian Dental Journal, vol. 52, No. 2, 2007, pp. 133-137.

Mount, GJ, "A new paradigm for operative dentistry.", Australian Dental Journal vol. 52, No. 4, 2007, pp. 264-270.

Murata et al., "Remineralization Power by Xylitol Chewing Gums", Abstract 2046—82nd General Session of the IADR, 2004, Honolulu, Hawaii. Abstract only.

Narayana, T. et al. "An in vitro study of wear prevention in dentine." Abstract 2424—84th General Session of the IADR, Jun. 28-Jul. 1, 2006, Brisbane, Australia.

Ng, H. et al. "Aesthetic management of severely fluorosed incisors in an adolescent female." Australian Dental Journal, vol. 52, No. 3, 2007, pp. 243-248.

O'Hehir, T "Caries—More than a filling.", Hygientown.com, Jul./Aug. 2008, pp. 8-12.

Ono et al., "Complexes of Casein Phosphopeptide and Calcium Phosphate Prepared from Casein Micelles by Tryptic Digestion", Biosci. Biotech. Biochem. 58 (8), pp. 1376-1380, 1994.

Ono et al., "Preparation of Casein Phosphopeptides from Casein Micelles by Ultrafiltration", Biosci. Biotech. Biochem. 59 (3), pp. 510-511, 1995.

Oshiro, M. et al. "Effect of CPP-ACP paste on tooth mineralization: an FE-SEM study." Journal of oral Science, vol. 49, No. 2, 2007, pp. 115-120.

Perdigao, J. et al. "Contemporary Trends and Techniques in Tooth Whitening: A Review", Practical Procedures & Aesthetic Dentistry, vo. 16, No. 3, 2004, pp. 185-192.

Perich et al., "Efficient Solution-Phase Synthesis of Multiple O-Phosphoseryl-Containing Peptides Related to Casein and Statherin", Int. J. Pept. Protein Res. (Aug. 1992), 40:2 pp. 81-88.

Perich et al., "The Use of Synthetic Phosphopeptides for Epitope Mapping of the ASI-Casein Phosphopeptide Segment 59-70", Bioorg. Med. Chern. Lett. (1992), 2: pp. 1153-1154.

Peschke, J.C. et al. "Nucleating Ability of Calcium Phosphate-Protein-Composites.", Abstract 2244, IADR Mar. 2007, New Orleans, USA.

Piekarz, C. et al. "An in vitro assessment of the role of Tooth Mousse in preventing wine erosion.", Australian Dental Journal, vol. 53, 2008, pp. 22-25.

Pietrzycka, K. "Chemical methods of treatment of dental caries: the action and application of CPP-ACP.", E-Dentico, vol. 2, No. 18, 2008, pp. 68-74. English Abstract.

Pitts, N.B. "Are we ready to move from operative to non-operative/preventive treatment of dental caries in clinical pmctice?", Caries Res, vol. 38, 2004, pp. 294-304.

(56) References Cited

OTHER PUBLICATIONS

Plate, U. et al. Investigation of the early mineralization on collagen in dentine of rat incisors by quantitative electron spectroscopic diffraction (ESD), Cell Tissue Res, vol. 278, 1994, pp. 543-547.
Poitevin et al., "Clinical Effectiveness of a CPP-ACP Creme for Tooth Hypersensitivity Treatment", EADR Istanbul, (Aug. 24-28, 2004), Abstract 0136.
Products for the dental hygienist—Desensitizers. The Dental Advisor, vol. 23, No. 6, Jul./ Aug. 2006.
Quartarone, E. "Surface kinetic roughening caused by dental erosion: an atomic force microscopy study.", Journal of Applied physics, vol. 103, 2008, 104702, 1-6.
Rahiotis, C. et al. "Effect of a CPP-ACP agent on the demineralization and remineralization of dentine in vitro.", Journal of Dentistry, vol. 35, 2007, pp. 695-698.
Rahiotis, C. et al. "Characterization of oral films formed in the presence of a CPP-ACP agent: An in situ study.", Journal of dentistry, vol. 36, 2008, pp. 272-280.
Ramadas, "The oral care for children with malignancies"; Synopses; Synopses: The Newsletter of the Australian and New Zealand Society of Paediatric Dentistry, Winning 2003 Postgraduate Essay; 28:1-20 (Mar. 2004).
Ramalingam et al., "An in Vitro Investigation of the Effects of Casein Phosphopeptide-Stabilized Amorphous Calcium Phosphate (CPP-ACP) on Erosion of Human Dental Enamel by a Sports Drink", IADR, General Session, San Diego (2002), Abstract 2810.
Ramalingam et al., "Erosion of Human Dental Enamel by Sports Drinks", Synopses 27:16-19, (2003).
Ramalingam, L. et al. "Adding Caesin Phosphopetide-amorphous Calcium Phosphate to Sports Drinks to Eliminate In Vitro Erosion.", Pediatric Dentistry, vol. 27, No. 1, 61-67, 2005.
Ranjitkar, S. et al. Enamel wear prevention under conditions simulating bruxism and acid regurgitation. Abstract 2428—84th General Session of the IADR, Jun. 28-Jul. 1, 2006, Brisbane, Australia.
Ranjitkar, S. et al. "The Role of Tooth Mousse in preventing enamel wear.", Poster 0375—session 39—42nd annual meeting of IADR—Continental European and Israeli Divisions, Sep. 26-29, 2007.
Ranjitkar, S. et al. "The role of tooth mousse in reducing erosive tooth wear.", Abstract 2500, Jul. 2008, International Association for Dental Research, Toronto, Canada.
Rees, J. et al. "Pronamel and tooth mousse: An initial assessment of erosion prevention in vitro.", Journal of Dentistry, vol. 35, 2007, pp. 355-357.
Reeves et al., "Calcium Phosphate Sequestering Phosphopeptide from Casein." Science. vol. 128, p. 472 (1958).
Reich, E. "Das kleine gewisse Etwas zur Remineralisation", Zahnmedizin, vol. 95, No. 21, 2-9, 2005. English Abstract.
Reich, E. "Flüssiger Zahnschmelz." Dental Magazine. 2005. English Abstract.
Reich, E. Dental Products Report Europe, Jan. 1, 2006.
Reich, E. "GC Tooth Mousse—Ein neuer Ansatz zur Remineralisation", Kongress: Wissenschaft und Praxis der Sanften Zahnheilkunde, Lindau am Bodensee, Mar. 3-4, 2006. English Abstract.
Reich, E. "Die Betreuung von Kariespatienten in der Praxis", Quintessenz, vol. 59, No. 12, 2008, pp. 1301-1307. English Abstract.
Reynolds et al., "A Review of the Effect of Milk on Dental Caries", Aust. J. Dairy Tech., 34, pp. 175-179 (Dec. 1979).
Reynolds et al., "Effect of Milk on Caries Incidence and Bacterial Composition of Dental Plaque in the Rat", Arch Oral Biol. (1981) 26:5 pp. 445-51.
Reynolds et al., (1982) Phosphoprotein inhibition of hydroxapatite dissolution. Calcif. Tissue Int. 34: S52-S56.
Reynolds et al., (1983) Effect of adsorbed protein on hydroxyapatite zeta potential and *Streptococcus mutans* adherence. Infection and Immunity 39(3): 1285-1290.
Reynolds et al., (1984) Effect of casein and whey-protein solutions on caries experience and feeding patterns of the rat. Arch. Oral. Biol. 29(11): 927-933.
Reynolds et al., (1987) Confectionary composition and rat caries. Caries Res. 21: 538-545.
Reynolds et al., (1987) Reduction of chocolate's cariogenicity by supplementation with sodium caseinate. Caries Res. 21: 445-451.
Reynolds, (1987) The prevention of sub-surface demineralization of bovine enamel and change in plaque composition by casein in an intra-oral model. J. Dental Res. 66(6): 1120-1127.
Reynolds et al., "Cariogenicity of a Confection Supplemented with Sodium Caseinate at a Palatable Level." Caries. Res. vol. 23. pp. 368-70 (1989).
Reynolds et al., (1989), Protein dissimilation by human salivary-sediment bacteria. J. Dent.Res. 68:124-129.
Reynolds et al., "A Selective Precipitation Purification Procedure for Multiple Phosphoseryl-Containing Peptides and Methods for Their Identification", Anal. Biochem., (Mar. 1994), 217:2, pp. 277-284.
Reynolds, et al., "Anticariogenicity of Calcium Phosphate Complexes of Tryptic Casein Phosphopeptides in the Rat," *J Dent Res*, 74(6): 1272-1279 (1995).
Reynolds, E.C. "Dairy Products and Dental Health," *Proceedings of the Nutrition Society of Australia* pp. 95-102 (1995).
Reynolds, E. C., "Remineralization of Enamel Subsurface Lesions by Casein Phosphopeptide-stabilized Calcium Phosphate Solutions," *J Dent Res.*, 76:9 1587-1595 (1997).
Reynolds, 1998, "Anticariogenic complexes of amorphous calcium phosphate stabilized by casein phosphopeptides: A review." Journal of Special Care in Dentistry, vol. 18:1, pp. 8-16.
Reynolds et al., "Advances in Enamel Remineralization: Anticariogenic Casein Phosphopeptide-Amorphous Calcium Phosphate", J. Clin. Dent. (1999), X(2): pp. 86-88.
Reynolds, "Anticariogenic Casein Phosphopeptides", Prot. Peptide Lett. (1999), pp. 295-303.
Reynolds, "The Role of Phosphopeptides in Caries Prevention", Dental Perspectives (1999), 3, pp. 6-7.
Reynolds et al., "Enamel Remineralization by Chewing Gum Containing Casein Phosphopeptide-Amorphous Calcium Phosphate", IADR, General Session, Chiba, Abstract 0489, (2001).
Reynolds, "Caries Prevention and Oral Health", Health Aspects of Dairy Products/Caries Prevention and Oral Health, 2002. pp. 1306-1313.
Retention in Plaque and Remineralization of Enamel Lesions by Various Forms of Calcium in a Mouthrinse or Sugar-Free Chewing Gum. School of Dental Science, The University of Melbourne pp. 1-24.
Reynolds, EC. "Remineralization of early enamel caries by anticariogenic casein phosphopeptide-amorphous calcium phosphate nanocomplexes." Dental Practice Nov./Dec. 2001, 3 pages.
Reynolds, "Dairy Components in Oral Health", Aust. J. Dairy Tech. 58: pp. 79-81, (2003).
Reynolds et al., "Retention in Plaque and Remineralization of Enamel Lesions by Various Forms of Calcium in a Mouthrinse or Sugar-free Chewing Gum," J Dent Res 82(3): 206-211, 2003.
Reynolds et al. "Additional Aids to the Reminersalisation of Tooth Structure," Preservation and Restoration of Tooth Structure Chapter 8, 111-118, 2005.
Reynolds, E. C. et al. "Improved plaque uptake and enamel remineralization by fluoride with CPP-ACP." Abstract 2538—84th General Session of the IADR, Jun. 28-Jul. 1, 2006, Brisbane, Australia.
Reynolds, E. "Calcium phosphate-based remineralizatron systems: scientific evidence?" Australian Dental Journal, vol. 53, 2008, pp. 268-273.
Reynolds, EC et al. "Fluoride and casein phosphopeptide-amorphous calcium phosphate.", J Dent Res vol. 87, No. 4, 2008, pp. 344-348.
Roberts, "Role of Models in Assessing New Agents for Caries Prevention-Non-Fluoride Systems", Adv. Dent. Res. (Nov. 1995), 9(3), pp. 304-11; discussion 312-314.
Roberts MJ et al. "Remineralisation of fluorotic enamel lesions by casein phosphopeptide-amorphous calcium fluorophosphate (CPP-ACFP) solution." IADR,ANZ division, Abstract 54, 2000.
Robinson et al. "Effect of Surface Zone Deproteinisation on the Access of Mineral Ions into Subsurface Carious Lesions of Human Enamel", Caries Res 1990; 24:226-230.

(56) References Cited

OTHER PUBLICATIONS

Rose, "Binding Characteristics of *Streptococcus mutans* for Calcium and Casein Phosphopeptide", Caries. Res. (2000), 34, pp. 427-431.

Rose, "Effects of an Anticariogenic Casein Phosphopeptide on Calcium Diffusion in Streptococcal Model Dental Plaques", Arch Oral Bioi, vol. 45, Issue 7, (2000) pp. 569-575.

Rosen et al., "Effect of Cheese, With and Without Sucrose, On Dental Caries and Recovery of *Streptococcus mutans* in Rats", J. Dent. Res. 63: pp. 894-96, (1984).

Rozwadowska, E. "Children and private dentistry." Private Dentistry, May 2006, pp. 109-113.

Sakaguchi, Y. et al. "Preventing acid induced enamel demineralization using CPP-ACP containing paste." Abstract 2055—IADR, Mar. 2005, Baltimore, Maryland, USA.

Sakaguchi, Y. et al. "Remineralization potential of CPP-ACP and its synergy with fluoride.", Abstract 191—84th General Session of the IADR, Jun. 28-Jul. 1, 2006, Brisbane, Australia.

Sato et al. "Caries prevention Potential of a Tooth-coating Material Containing Casein Phospho peptide-Amorphous Calcium Phosphate (CPP-ACP)," IADR, General session, Goteborg, 2003, Abstract 1007.

Schüpbach et al., "Incorporation of Caseinoglycomacropeptide and Caseinophosphopeptide into the Salivary Pellicle Inhibits Adherence of Mutans Streptococci", J. Dent. Res, vol. 75, pp. 1779-1788, (1996).

Schweigert, BS et al. "Dental caries in the cotton rat. VI. The effect of the amount of protein, fat and carbohydrate in the diet on the incidence and extent of carious lesions". J. Nutr., vol. 31, 1946, pp. 439-447.

Shaw JH "Effects of dietary composition on tooth decay in the albino rat." J. Nutr. 41, 1950, pp. 13-23.

Sheharyar, S. et al. "Efficacy of MI Paste For Sensitivity Associated With Vital Bleaching.", Abstract 2041, IADR Mar. 2007, New Orleans, USA.

Shen et al., "Remineralization of Enamel Subsurface Lesions by Sugar-free Chewing Gum Containing Casein Phosphopeptide-Amorphous Calcium Phosphate," J Dent Res 80(12):2066-2070, 2001.

Shen et al., "Enamel remineralization by a mouthrinse containing casein phosphopeptide-amorphous calcium phosphate and fluoride in an in situ model"; Australian Dental Journal ADRF; Special Research Supplement, 49(4):S19 (2004).

Shen, P. et at. "Remineralization by a mouthrinse containing CPP-ACP at pH 5.5.", Abstract 189—84th General Session of the IADR, Jun. 28-Jul. 1, 2006, Brisbane, Australia.

Shen, P. et al. "Remineralization of Enamel Subsurface Lesions by Sugar-free Chewing Gum Containing Casein Phosphopeptide-Amorphouse Calcium Phosphate." School of Dental Science, The University of Melbourne. Research Reports. pp. 266-270.

Silva et al., "Effects of Water-soluble Components of Cheese on Experimental Caries in Humans," J Dent Res 66(1):38-41, Jan. 1987.

Silva, Margarita et al. "Fluoride content of infant formulae in Australia." Australian Dental Journal 1996:41:1.

Slomiany, B. et al. "Salivary Mucins in Oral Mucosal Defense", Gen. Pharmac., vol. 27, No. 5, 1996, pp. 761-771.

Smith, S. "Ultramorphological evaluation of dentin after treatment with different desensitizing agents.", Abstract 0941, IADR 2007, New Orleans, USA.

Smolenski, D. et al. "MI Paste and Fluoride for Caries Prevention In-Vitro.", Abstract 0505, IADR 2007, New Orleans, USA.

Steinberg, S. "A modern paradigm for caries management, Part 1: Diagnosis and Treatment." Dentistry Today, Feb. 2007.

Steinberg, S. "A modern paradigm for caries management, Part 2: A practical protocol." Dentistry Today, Jun. 2007.

Stößer, L. "Kariesprotektive Eigenschaften des durch Caseinphosphopeptid stabilisierten amorphen Calciumphosphat-Nanokomplexes (CPP-ACP)",. Deutsche Zahniirztliche Zeitschrift, 62-2007-9, 2007. Abstract.

Sudjalim, T.R. et al. "Prevention of white spot lesions in orthodontic practice: a contemporary review.", Australian Dental Journal, vol. 51, No. 4, 2006, pp. 284-289.

Sudjalim, T.R. et al. Prevention of demineralization around orthodontic brackets in vitro. American Journal of Orthodontics and Dentofacial Orthopedics., 2007, 131, 6, pp. 705.e1-705. e9.

Sukasaem, H. et al. "Effect of CPP-ACP on hardness of enamel eroded by Cola-drink." Abstract 1673—84th General Session of the IADR, Jun. 28-Jul. 1, 2006, Brisbane, Australia.

Takamizawa, T et al. "Determination of demineralization of tooth substrate by use of an ultrasonic device." Japan J Conserv Dent Jun vol. 47 Spring Issue 24—Abstract B-4, 2004.

Talbo et al., "MALDI-PSD-MS Analysis of the Phosphorylation Sites of Caseinomacropeptide", Peptides (Jul. 2001) 22:7, pp. 1093-1098.

Tantbirojn, D. et al. "Changes in surface hardness of enamel by a cola drink and CPP-ACP paste.", Journal of Dentistry, vol. 36, 2008, pp. 74-79.

Ten Cate, Jacob M. "Current concepts on the theories of the mechanism of action offluoride." Acta Odontol, Scand 57 (1999), 325-329.

Theerapiboon, U. et al. "Remineralization of artificial caries by CPP-ACP paste.", Abstract 3274, Jul. 2008, International Association for Dental Research, Toronto, Canada.

Trajtenberg, C.P. et al. "CPP-ACP Paste with Fluoride: In Vitro Root Surface Caries Formation.", Abstract 0500, IADR 2007 New Orleans, USA.

Translation of Russian Office Action from Application No. 2007123603, dated 2007.

Translation of Russian Office Action from Application No. 2007123603, dated May 26, 2009.

Turssi, C.P. et al. "Progression of erosion following use of calcium and phosphorus compounds.", Abstract 2499, Jul. 2008, International Association for Dental Research, Toronto, Canada.

Ung, M. et al. "Investigation of the binding of casein phosphopeptides to the major enamel pellicle proteins.", Australian Dental Journal ADRF Special Research Supplement vol. 49, No. 4, S19-S20, 2004.

Vlacic et al., "Combined CPP-ACP and photoactivated disinfection (PAD) therapy in arresting root surface caries: a case report"; British Dental Journal; 203(8):457-459 (2007).

Walker, Glen et al. "Increased remineralization of tooth enamel by milk containing added casein phosphopeptide amorphous calcium phosphate." Journal of Dairy Research (2006) 73, pp. 74-78.

Walsh, L.J. et al. "Effect of CPP-ACP versus potassium nitrate on cervical dentinal hypersensitivity.", Abstract 947—84th General Session of the IADR, Jun. 28-Jul. 1, 2006, Brisbane, Australia.

Walsh, L. "Application of the System for Total Environmental Management(STEM) to demineralization, dental erosion and tooth wear.", Australasian Dental Practice, Jan.-Feb. 2008, pp. 5258.

Walsh, L.J. "The effects of GC Tooth Mousse on cervical dentinal sensitivity: a controlled clinical trial", International Dentistry SA—Australasian Edition vol. 12, No. 1, 4-12, 2010.

Weiss, Dr. V. "Kariesprophylaxe in der kinderzahnnarztlichen Praxis", ZWP, Oct. 2005, 18 pp. 76-79. English Abstract.

Westerman, G. et al. "Argon Laser and Remineralizing Paste Effect on Root Surface Caries.", Abstract 0018, IADR Mar. 2007, New Orleans, USA.

Westerman, G. et al. "The Argon Laser and Remineralizing Paste with Fluoride Effects on Enamel Caries." AAPD, Washington, 2008.

White, "Use of Synthetic Polymer Gels for Artificial Carious Lesion Preparation" Caries Research 21, 1987, pp. 228-242. Abstract Only.

Wilfershausen, B. et al. "In-Vitro-Studie Zur Überprüfung einermöglichen Remeralisation durch caesinphosphopetidhaltige Calciumphosphat-komplexe (CPP ACP).", Deutsche Zahnarztiche Zeitschrift, vol. 63, No. 2, 2008, pp. 134-139. English Abstract.

Wilkiel, et al., "Hydroxyapatite Mineralization and Demineralization in the Presence of Synthetic Phosphorylated Pentapeptides," Archives of Oral Biology, 39:8, 715-721 (1994).

William, V. et al. "Molar Incisor Hypomineralization: Review and Recommendations for Clinical Management", Pediatric Dentistry, vol. 28, No. 3, 224-232, 2006.

Wong, L, et al. "Plaque microcosm biofilm mineralization by CPP-ACP and calcium-phosphatemonofluorophosphate-urea min-

(56) References Cited

OTHER PUBLICATIONS eralizing solution." Abstract 1269—84th General Session of the IADR, Jun. 28-Jul. 1, 2006, Brisbane, Australia.
Wong, R. et al. Incorporation of casein phosphopeptide-amorphous calcium phosphate into a temporary cement. Abstract 0653—84th General Session of the IADR, Jun. 28-Jul. 1, 2006, Brisbane, Australia.
Wright, S. et al. "Artificial Caries Inhibited with MI Paste and Two Restorative Materials.", Abstract 2777, IADR 2007, New Orleans, USA.
Xie, Q. et al. "Remineralization Effects of CPP-ACP and Proanthocyanidin on Artificial Root Caries.", Abstract 0512, IADR 2007, New Orleans, USA.
Yamaguchi, K. et al. "Effect of CPP-ACP paste on mechanical properties of bovine enamel as determined by an ultrasonic device.", Journal of Dentistry, vol. 34, 2006, pp. 230-236.
Yamaguchi, K. et al. "Ultrasonic determination of the effect of casein phosphopeptide-amorphous calcium phosphate paste on the demineralization of bovine dentin.", Caries Res, vol. 41, 2007, pp. 204-207.
Zero, DT "In situ caries models." Adv Dent Res vol. 9(3), 1995, pp. 214-230.
Zhang, L, et al. "Experimental study of phosphopeptide in promoting tooth remineralisation." Chinese J Dent Res., vol. 3(1), May 2000, pp. 27-30.
Zhao et al. "The remineralization for enamel lesions by casein phosphopeptide-amorphous calcium fluoride phospate in vitro." Zhonghua Kou Qiang Yi Kxue Za Zhi. vol. 36. No. 6. 2001. pp. 421-423, with English translation.
"Tooth Mousse." Pierre qui roule n'amasse pas mousse? Ben si! Clinic—Avril 2006—vol. 27, p. 218-219, English Abstract provided.
"Putting mouths where the money is.", DPRAsia, Jan./Feb. 2007, pp. 8-10.
"GC Tooth Mousse—Eine ganz andere Art der Prevention." Dental Spiegel, Feb. 2005, pp. 53-54. English Abstract.
GC stellt Kasein-haltige Zahnschutzcreme vor—Vorbeugen staff reparieren DZW Special IDS-Nachlese. 2005. English Abstract, pp. 10-11.
"Tradition and modemes know how—ein Erfolgsrezept.", Zahn Prax 8, vol. 5, 2005, p. 267. English Abstract.
Preventive agents; The Dental Advisor; 21(10):1-5 (Dec. 2004).
"Caseine phosphopeptide et phosphate de calcium amorphe: un complexe prometteur.", Dialogue dentaire, Printemps 2005/W30, pp. 27-29. English Abstract provided.

"Colorimetry" Second Edition. By CIE Technical Committee. CIE 1986.
"Editors' Choice—Prospec MI Paste." The Dental Advisor, vol. 22, No. 5, Jun. 2005.
Minimale Intervention für maximale Mundgesundheit., DZW Special. Mar. 2005. English Abstract.
Akinamade et al., "Review Glass-Ionomer Cements as Adhesives, Part I, Fundamental Aspects and Their Clinical Relevance," Journal of Materials Science: Materials in Medicine, vol. 4, pp. 95-101 (1993).
Basting RT et al., "The Effect of 10% Carbamide Peroxide Bleaching Material on Microhardness of Sound and Demineralized Enamel and Dentin In Situ" {Clinical Research} Operative Dentistry, 26: 531-529 (2001).
Calcium Glycerophosphate, DrugBank, pp. 1-5, XP002783472 (created Mar. 12, 2015) (retrieved Jul. 31, 2018).
Colgate Fluoride Conversions colgate professional.com Feb. 2013.
de Oliveira et al., "In situ effect of a CPP-ACP chewing gum on enamel erosion associated or not with abrasion", Clin Oral Investig. 21:339-346 (2016).
Haywood VB et al., History, safety, and effectiveness of current bleaching techniques and applications of the nightguard vital bleaching technique Quintessence Int. 23(7): 471-88 (Jul. 1992).
Imfeld et al, "Prevention of progression of dental erosion by professional and individual prophylactiv measures," Eur J Oral Sci (1996) 104:215-220
Mellberg, J.R. et al. "Effect of soluble calcium on fluoride uptake by enamel from sodium monofluorophosphate" J Dent Res. 1982 vol. 61, No. 12, pp. 1394-1396.
Mitthra et al., "Mineral Loss before and after Bleaching and Mineral Uptake on Application of Remineralizing Agent", Indian Journal of Multidisciplinary Dentistry and Endodontics, vol. I, No. 1, Jan. 2010.
Pelletier et al., "Study of the Hyrolyisis Reaction of the PA3F2 Anion in Aqueous Solution," Z. Anorg. Alig. Chem., 581: 190-198 (1990).
Tay et al. "Assessing the Effect of a Desensitizing Agent Used Before In-office Tooth Bleaching," The Journal of the American Dental Association, vol. 140, Issue 10, (Oct. 2009); pp. 1245-1251.
Translation of Japanese Office Action from Application No. 2002-590925, dated Nov. 18, 2008.
Walker et al.., "Consumption of milk with added casein phosphopeptide-amorphous calcium phosphate remineralizes enamel subsurface lesions in situ," Australian Dental Journal, vol. 54, No. 3, pp. 245-249, Sep. 2009.
Walsh, L., "Tooth Mousse Information", GC Tooth Mousse Portfolio 2nd Edition, Mar. 2005.

\* cited by examiner

(A)

Before treatment with stabilized SnF$_2$/ACP

(B)

After treatment with stabilized SnF$_2$/ACP showing the novel surface layer (arrow)

(A)

(B)

```
                         SEQUENCE LISTING

<160> NUMBER OF SEQ ID NOS: 4

<210> SEQ ID NO 1
<211> LENGTH: 21
<212> TYPE: PRT
<213> ORGANISM: Bos sp.
<220> FEATURE:
<221> NAME/KEY: MISC_FEATURE
<222> LOCATION: (6)..(6)
<223> OTHER INFORMATION: Phosphorylated serine residue
<220> FEATURE:
<221> NAME/KEY: MISC_FEATURE
<222> LOCATION: (8)..(10)
<223> OTHER INFORMATION: Phosphorylated serine residue
<220> FEATURE:
<221> NAME/KEY: MISC_FEATURE
<222> LOCATION: (17)..(17)
<223> OTHER INFORMATION: Phosphorylated serine residue

<400> SEQUENCE: 1

Gln Met Glu Ala Glu Xaa Ile Xaa Xaa Xaa Glu Glu Ile Val Pro Asn
1               5                   10                  15

Xaa Val Glu Gln Lys
            20

<210> SEQ ID NO 2
<211> LENGTH: 25
<212> TYPE: PRT
<213> ORGANISM: Bos sp.
<220> FEATURE:
<221> NAME/KEY: MISC_FEATURE
<222> LOCATION: (15)..(15)
<223> OTHER INFORMATION: Phosphorylated serine residue
<220> FEATURE:
<221> NAME/KEY: MISC_FEATURE
<222> LOCATION: (17)..(19)
<223> OTHER INFORMATION: Phosphorylated serine residue

<400> SEQUENCE: 2

Arg Glu Leu Glu Glu Leu Asn Val Pro Gly Glu Ile Val Glu Xaa Leu
1               5                   10                  15

Xaa Xaa Xaa Glu Glu Ser Ile Thr Arg
            20                  25

<210> SEQ ID NO 3
<211> LENGTH: 25
<212> TYPE: PRT
<213> ORGANISM: Bos sp.
<220> FEATURE:
<221> NAME/KEY: MISC_FEATURE
```

```
<222> LOCATION: (11)..(13)
<223> OTHER INFORMATION: Phosphorylated serine residue
<220> FEATURE:
<221> NAME/KEY: MISC_FEATURE
<222> LOCATION: (16)..(16)
<223> OTHER INFORMATION: Phosphorylated serine residue

<400> SEQUENCE: 3

Asn Ala Asn Glu Glu Glu Tyr Ser Ile Gly Xaa Xaa Xaa Glu Glu Xaa
1               5                   10                  15

Ala Glu Val Ala Thr Glu Glu Val Lys
            20                  25

<210> SEQ ID NO 4
<211> LENGTH: 21
<212> TYPE: PRT
<213> ORGANISM: Bos sp.
<220> FEATURE:
<221> NAME/KEY: MISC_FEATURE
<222> LOCATION: (8)..(10)
<223> OTHER INFORMATION: Phosphorylated serine residue
<220> FEATURE:
<221> NAME/KEY: MISC_FEATURE
<222> LOCATION: (16)..(16)
<223> OTHER INFORMATION: Phosphorylated serine residue

<400> SEQUENCE: 4

Lys Asn Thr Met Glu His Val Xaa Xaa Xaa Glu Glu Ser Ile Ile Xaa
1               5                   10                  15

Gln Glu Thr Tyr Lys
            20
```

STABILIZED STANNOUS COMPOSITIONS

SEQUENCE LISTING

The instant application contains a Sequence Listing which has been submitted electronically in ASCII format and is hereby incorporated by reference in its entirety. Said ASCII copy, created on Nov. 22, 2020, is named 50133831_ST25.txt and is 2,252 bytes in size.

FIELD OF THE INVENTION

The present invention relates to improved complexes of amorphous calcium phosphate and/or amorphous calcium fluoride phosphate stabilised by phosphopeptides/phosphoproteins by addition of stannous ions. These complexes have anticariogenic properties useful to protect tooth structures as they remineralize (repair) early stages of dental caries and have other dental/medical applications (including anti-calculus, anti-erosion/corrosion and anti-dentinal hypersensitivity). Methods of making the complexes of the invention and of treatment or prevention of various dental conditions including dental caries, dental calculus, dental erosion/corrosion and dental hypersensitivity are also provided.

This application claims priority to Australian patent application nos. 2013905081, 2014901202 and 2014903815, these applications are incorporated by reference in their entirety.

BACKGROUND OF THE INVENTION

Common causes of hypomineralized lesions are caries and fluorosis.

Dental caries is initiated by the demineralization of hard tissue of the teeth usually by organic acids produced from fermentation of dietary sugar by dental plaque odontopathogenic bacteria. Dental caries is still a major public health problem. Further, restored tooth surfaces can be susceptible to further dental caries around the margins of the restoration. Even though the prevalence of dental caries has decreased through the use of fluoride in most developed countries, the disease remains a major public health problem. Dental erosion or corrosion is the loss of tooth mineral by dietary or regurgitated acids. Dental hypersensitivity is due to exposed dentinal tubules through loss of the protective mineralized layer, cementum. Dental calculus is the unwanted accretion of calcium phosphate minerals on the tooth surface. All these conditions, dental caries, dental erosion, dental hypersensitivity and dental calculus are therefore imbalances in the level of calcium phosphates.

Enamel fluorosis (mottling) has been recognized for nearly a century, however, the aetiological role of fluoride was not identified until 1942 (Black and McKay, 1916). The characteristic appearance of fluorosis may be differentiated from other enamel disturbances (Fejerskov et al., 1991). The clinical features of fluorotic lesions of enamel (FLE) represent a continuum ranging from fine opaque lines following the perikymata, to chalky, white enamel (Fejerskov et al., 1990; Giambro et al., 1995). The presence of a comparatively highly mineralized enamel outer surface and a hypomineralized subsurface in the fluorotic lesion simulates the incipient enamel "white spot" carious lesion (Fejerskov et al., 1990). With increasing severity, both the depth of enamel involved in the lesion and the degree of hypomineralization increases (Fejerskov et al., 1990, Giambro et al., 1995). The development of fluorosis is highly dependent on the dose, duration and timing of fluoride exposure (Fejerskov et al., 1990, Fejerskov et al., 1996; Aoba and Fejerskov, 2002) and is believed to be related to elevated serum fluoride concentrations. Chalky "white spot" lesions may also form on developing teeth in children such as after treatment with antibiotics or fever. Such lesions indicate areas of hypomineralization of the tooth enamel.

Depending on lesion severity, fluorosis has been managed clinically by restorative replacement or micro-abrasion of the outer enamel (Den Besten and Thariani, 1992; Fejerskov et al., 1996). These treatments are unsatisfactory because they involve restorations or removal of tooth tissue. What is desired is a treatment that will mineralize the hypomineralized enamel to produce a natural appearance and structure.

Specific complexes of casein phosphopeptides and amorphous calcium phosphate ("CPP-ACP", available commercially as Recaldent™) have been shown to remineralize enamel subsurface lesions in vitro and in situ (Reynolds, 1998; Shen et al., 2001; Reynolds et al., 2003).

WO 98/40406 in the name of The University of Melbourne (the contents of which are herein incorporated fully by reference) describes casein phosphopeptide-amorphous calcium phosphate complexes (CPP-ACP) and CPP-stabilised amorphous calcium fluoride phosphate complexes (CPP-ACFP) which have been produced at alkaline pH. Such complexes have been shown to prevent enamel demineralization and promote remineralization of enamel subsurface lesions in animal and human in situ caries models (Reynolds, 1998). The CPP which are active in forming the complexes do so whether or not they are part of a full-length casein protein. Examples of active (CPP) that can be isolated after tryptic digestion of full length casein have been specified in U.S. Pat. No. 5,015,628 and include peptides Bos $\alpha_{s1}$-casein X-5P (f59-79) [1], Bos β-casein X-4P (f1-25) [2], Bos $\alpha_{s2}$-casein X-4P (f46-70) [3] and Bos $\alpha_{s2}$-casein X-4P (f1-21) [4]. Moreover, improvements on these compositions are disclosed in WO 2006/056013 and WO 2007/090242 and specific uses (the contents of which are herein incorporated fully by reference).

Stannous fluoride ($SnF_2$) is one of a number of metal fluoride salts that has been proposed as an anticaries and antiplaque agent however there are difficulties in delivering this agent in toothpaste, mouthwash and other oral care products due to the instability of the stannous ions. In the presence of hydroxide ions and phosphate ions stannous can precipitate as stannous hydroxide and stannous phosphate complexes. This precipitate is significantly less biologically available and can be more easily removed from the oral cavity by swallowing. Furthermore the stannous ions can be oxidized to Stannic ions (SnIV) which are even more reactive to produce poorly soluble forms with very low activity. New toothpaste formulations with $SnF_2$ rely on being non-aqueous or use polyphosphate to stabilize the stannous ions. However, these formulations have low acceptance particularly by people with dry mouth. There is a need to provide improved or alternative treatments for hypomineralized lesions.

Reference to any prior art in the specification is not, and should not be taken as, an acknowledgment or any form of suggestion that this prior art forms part of the common general knowledge in Australia or any other jurisdiction or that this prior art could reasonably be expected to be ascertained, understood and regarded as relevant by a person skilled in the art.

SUMMARY OF THE INVENTION

In one aspect, the invention provides a stannous-associated stabilized amorphous calcium phosphate (ACP) and/or amorphous calcium fluoride phosphate (ACFP) complex.

The stannous may be bound to the stabilized amorphous calcium phosphate (ACP) and/or amorphous calcium fluoride phosphate (ACFP) as determined using the experimental protocol in Example 2. In one embodiment, stannous-associated stabilized amorphous calcium phosphate (ACP) and/or amorphous calcium fluoride phosphate (ACFP) complex are produced by the method as described herein, including but not limited to the method described in Example 1.

Without being bound by any theory or mode of action, it is believed that phosphopeptides, such as casein phosphopeptides, can stabilize a stannous compound in an aqueous environment and in the presence of stabilized amorphous calcium phosphate (ACP) and stabilized amorphous calcium fluoride phosphate (ACFP) these complexes are superior to other forms of fluoride and stabilized ACP or ACFP in remineralizing enamel subsurface lesions. Mineralization of dental surfaces can be significantly enhanced by providing a stannous compound during the process of mineralization by stabilized ACP and/or stabilized ACFP. In particular, it has been found that the mineralization of enamel by stabilized soluble forms of stannous-associated ACP complexes and stannous-associated ACFP complexes is enhanced compared with stabilized ACP and fluoride without associated stannous. In other words, the stannous ions complex with CPP-ACP and/or CPP-ACFP complexes, and these Sn-associated CPP-AC(F)P complexes then deliver superior properties. Various compositions incorporating these complexes for administration are useful. Where the fluoride stannous salt is used, additional fluoride ions are available in compositions of the stannous-associated ACP/ACFP complexes. Additional fluoride ions may also be provided by inclusion of NaF in the composition.

The invention also provides a stannous-associated stabilized ACP or ACFP having a stannous ion content of at least 1 mole of stannous per mole of phosphopeptide. Preferably, the stannous-associated stabilized ACP or ACFP has a stannous ion content of at least 2, 3, 4, 5, 6, 7, 8, 9 or 10 moles of stannous per mole of phosphopeptide. Even more preferably, the stannous ion content is in the range of 1 to 100, 1 to 50, 1 to 20 or 1 to 10 moles of stannous per mole of phosphopeptide. The present invention also provides a composition comprising, or consisting of, stannous-associated stabilized ACP and/or ACFP complexes as described herein.

In any embodiment, the stannous ion content above may be the stannous ion content tightly-bound to the complex (as described herein). In assessing the stannous ion content, the tightly-bound stannous ion content is measured by the methods described herein, in particular, in Example 6.

The invention also provides a stannous-associated stabilized ACP and/or ACFP complex comprising stannous ions that remain associated with the complex after centrifugation in a 1000 molecular weight cut off filter at about 3000 g for 1 hour at room temperature.

The invention also provides a stannous-associated stabilized ACP or ACFP having at least 50, 60, 65, 70, 75, 80, 85, 90, 91, 92, 93, 94, 95, 96, 97, 98, 99 or 100% of the stannous associated with the complex as tightly bound as determined by the method in Example 6.

The invention also provides a stannous-associated stabilized ACP or ACFP having at least 50, 60, 65, 70, 75, 80, 85, 90, 91, 92, 93, 94, 95, 96, 97, 98, 99 or 100% of the stannous used in preparing the complexes incorporated into the complexes. The complex may be prepared as outlined in Example 1.

In one embodiment the invention provides a stannous fluoride associated stabilized amorphous calcium phosphate (ACP) and/or a stannous fluoride associated amorphous calcium fluoride phosphate (ACFP) complex. In another aspect, invention provides a composition including a stannous compound and stabilized ACP or ACFP. In either embodiment, the stannous compound is preferably stannous fluoride and/or stannous chloride. Optionally, NaF is also included.

In one aspect, the present invention provides a method of mineralizing a dental surface or sub-surface comprising contacting the dental surface or subsurface with (a) a composition including a stannous compound and stabilized ACP or ACFP, or (b) a stannous-associated stabilized ACP or ACFP.

The stannous containing compound can be any soluble stannous containing compound suitable for oral use. Preferably, stannous containing compound is a stannous salt. The stannous salt may contain fluoride. A stannous salt includes, but not limited to, stannous fluoride, stannous chloride, potassium stannous fluoride, sodium stannous fluorozirconate, stannous chloride fluoride, stannous acetate, sodium stannous fluoride, stannous hexafluorozirconate, stannous sulfate, stannous tartrate, stannous gluconate, disodium monostannous citrate. Preferred stannous salts include stannous fluoride and stannous chloride The dental surface is preferably dental enamel or dentine. In one embodiment the dental surface is a lesion in the enamel, such as a lesion caused by caries, dental erosion or fluorosis. In another embodiment the surface is exposed dentine causing dentinal hypersensitivity.

Preferably, the stabilized amorphous calcium phosphate (ACP) and/or amorphous calcium fluoride phosphate (ACFP) is phosphopeptide stabilized. Preferably, the phosphopeptide (as defined below) is a casein phosphopeptide.

In a preferred embodiment, the phosphopeptide stabilised amorphous calcium phosphate (ACP) or amorphous calcium fluoride phosphate (ACFP) complex has tightly bound and loosely bound calcium, wherein the bound calcium in the complex is less than the tightly bound calcium in an ACP or ACFP complex formed at a pH of 7.0. Optionally, the ACP or ACFP is predominantly in a basic form.

In another aspect the invention also provides a composition including stannous-associated stabilized ACP or ACFP, further comprising fluoride, wherein fluoride is provided as stannous fluoride and sodium fluoride. Preferably, the composition includes 2% w/v stabilized ACP or ACFP, about 1100 ppm fluoride as stannous fluoride and about 350 ppm fluoride as sodium fluoride, or the composition includes 0.4% w/v stabilized ACP or ACFP, about 220 ppm fluoride as stannous fluoride and about 70 ppm fluoride as sodium fluoride. Preferably, the composition is a toothpaste.

In a preferred embodiment, the calcium ion content of the stabilised ACP or ACFP complex is in the range of about 30 to 100 moles of calcium per mole of PP. More preferably, the calcium ion content is in the range of about 30 to about 50 moles of calcium per mole of PP.

In a preferred embodiment the ACP and/or ACFP is in the form of a casein phosphopeptide stabilized ACP and/or ACFP complex.

Preferably, the phase of the ACP is primarily (i.e. >50%) a basic phase, wherein the ACP comprises predominantly the species $Ca^{2+}$, $PO_4^{3-}$ and $OH^-$. The basic phase of ACP may have the general formula $[Ca_3(PO_4)_2]_x[Ca_2(PO_4)(OH)]$ where $x \geq 1$. Preferably $x=1-5$. More preferably, $x=1$, i.e. the two components of the formula are present in equal proportions. Accordingly, in one embodiment, the basic phase of ACP has the formula $Ca_3(PO_4)_2Ca_2(PO_4)(OH)$.

Preferably, the phase of the ACFP is a primarily (i.e. >50%) basic phase, wherein the ACFP comprises predominantly the species $Ca^{2+}$, $PO_4^{3-}$ and $F^-$. The basic phase of ACFP may have the general formula $[Ca_3(PO_4)_2]_x[Ca_2(PO_4)]_y$, where $x \geq 1$ when $y=1$ or where $y \geq 1$ when $x=1$. Preferably, $y=1$ and $x=1-3$. More preferably, $y=1$ and $x=1$, i.e. the two components of the formula are present in equal proportions.

Accordingly, in one embodiment, the basic phase of ACFP has the formula $Ca_3(PO_4)_2Ca_2(PO_4)F$.

In one embodiment, the ACP complex consists essentially of phosphopeptides, calcium, phosphate and hydroxide ions and water.

In one embodiment, the ACFP complex consists essentially of phosphopeptides, calcium, phosphate, fluoride and hydroxide ions and water.

In a further aspect of the present invention there is provided a method of mineralizing a dental surface comprising providing (a) a composition including a stannous compound and stabilized ACP or ACFP, or (b) a stannous-associated stabilized ACP or ACFP. In a preferred embodiment the dental surface is enamel.

In a further aspect of the present invention there is provided a method of forming a layer on the surface of a tooth comprising providing (a) a composition including a stannous compound and stabilized ACP or ACFP, or (b) a stannous-associated stabilized ACP or ACFP. Preferably the tooth is in a subject identified as being susceptible to, or suffering from, any one or more of dental erosion, demineralization, caries or dentinal hypersensitivity. Preferably, the stabilized amorphous calcium phosphate (ACP) and/or amorphous calcium fluoride phosphate (ACFP) is phosphopeptide stabilized.

Preferably, the phosphopeptide (as defined below) is a casein phosphopeptide.

Such a layer may be characterised has a calcium:phosphate ratio equivalent to normal apatite, preferably where the ratio is about 2:1. The layer ideally contains an amount of calcium that is about 20 wt %.

Preferably, the layer has about 3 to 12 fold more stannous ions that sound enamel.

Preferably, the layer contains carbon, oxygen, fluoride, phosphate, calcium and stannous. The layer may exhibit about an elemental analysis of 20-30 wt % carbon, 35-45 wt % oxygen, 0.1-1 wt % fluoride, 8 to 12 wt % phosphate, 16 to 24 wt % calcium and/or 0.5-2 wt % stannous. Alternatively, the layer may exhibit an elemental analysis of any one of the elements, such as calcium, phosphate, fluoride, carbon and/or stannous, as shown in any one of Table 3 or 4.

In a further aspect of the present invention there is provided a process of forming a layer having a calcium:phosphate ratio at, or near, that of normal apatite on a dental surface, the process comprising contacting the dental surface with (a) a composition including a stannous compound and stabilized ACP or ACFP, or (b) a stannous-associated stabilized ACP or ACFP.

A method of protecting a tooth surface comprising providing (a) a composition including a stannous compound and stabilized ACP or ACFP, or (b) a stannous-associated stabilized ACP or ACFP. Typically the tooth surface may be one that has been identified as benefiting from a surface layer, for example, due to an increased likelihood of demineralization. The tooth surface may be an enamel surface or dentine surface.

In a further aspect of the present invention there is provided a method for treating fluorosis comprising contacting a fluorotic lesion in tooth enamel with (a) a composition including a stannous compound and stabilized ACP or ACFP, or (b) a stannous-associated stabilized ACP or ACFP.

In a further aspect of the present invention there is provided a method for treating dental caries comprising contacting a caries lesion in tooth enamel with (a) a composition including a stannous compound and stabilized ACP or ACFP, or (b) a stannous-associated stabilized ACP or ACFP.

In a further aspect of the present invention there is provided a method for treating dental erosion comprising contacting a lesion in tooth enamel caused by erosion with (a) a composition including a stannous compound and stabilized ACP or ACFP, or (b) a stannous-associated stabilized ACP or ACFP.

In a further aspect of the present invention there is provided a method for reducing dentinal hypersensitivity comprising contacting exposed dentine with (a) a composition including a stannous compound and stabilized ACP or ACFP, or (b) a stannous-associated stabilized ACP or ACFP.

In a further aspect of the present invention there is provided a method for remineralizing a lesion in tooth enamel or dentine comprising contacting the lesion with (a) a composition including a stannous compound and stabilized ACP or ACFP, or (b) a stannous-associated stabilized ACP or ACFP.

Preferably the stannous-associated stabilized ACP or ACFP are stabilized by a phosphopeptide (PP). In a preferred embodiment the phosphopeptide is a casein phosphopeptides. Preferably, the ACP or ACFP is in the form of a casein phosphopeptide stabilized ACP or ACFP complex.

In any aspect or embodiments as described herein, the stabilized ACP and/or ACFP or stannous-associated stabilized ACP or ACFP may be in a formulation with additional calcium phosphate. Typically, the formulation includes a PP stabilized ACP and/or ACFP complex together with at least an equal amount by weight of calcium phosphate.

In a further aspect of the invention there is provided a method for remineralizing a lesion in tooth enamel comprising contacting the lesion with (a) a composition including a stannous compound and stabilized ACP or ACFP, or (b) a stannous-associated stabilized ACP or ACFP followed by administering a composition containing sodium bicarbonate or urea. Preferably, the composition is a mouthrinse or mouthwash containing sodium bicarbonate or urea.

In any aspect or embodiment of the invention described herein, a compound which is capable of increasing or maintaining the pH of a solution may be administered concurrently with, as a pre-treatment to, or as a post-treatment to (a) a composition including a stannous compound and stabilized ACP or ACFP, or (b) a stannous-associated stabilized ACP or ACFP.

In any aspect or embodiment of the invention described herein, (a) a composition including a stannous compound and stabilized ACP or ACFP, or (b) a stannous-associated stabilized ACP or ACFP may be applied to the mouth, tooth or lesion by the subject in need of treatment or by a dental health care professional.

A composition including a stannous compound and stabilized ACP or ACFP may be contacted with the dental surface for a period of about 1 to 60 minutes, or for about 1 to 30 minutes. In one embodiment, a composition including a stannous compound and stabilized ACP/ACFP is contacted with the dental surface for about 20 minutes.

Preferably a composition including a stannous compound and stabilized ACP or ACFP is contacted with the dental surface for a period of about 1 minute to 2 hours, or 5 minutes to 60 minutes or about 10 minutes. The composition including a stannous compound and stabilized ACP/ACFP may be repeatedly applied to the dental surface over a period of 1 day to several months.

A stannous-associated stabilized ACP or ACFP may be contacted with the dental surface for a period of about 1 to 60 minutes, or for about 1 to 30 minutes. In one embodiment, a stannous-associated stabilized ACP/ACFP is contacted with the dental surface for about 20 minutes.

Preferably a stannous-associated stabilized ACP or ACFP is contacted with the dental surface for a period of about 1 minute to 2 hours, or 5 minutes to 60 minutes or about 10 minutes. The stannous-associated stabilized ACP or ACFP may be repeatedly applied to the dental surface over a period of 1 day to several months.

In one embodiment, (a) a composition including a stannous compound and stabilized ACP or ACFP, or (b) a stannous-associated stabilized ACP or ACFP, is contacted with the dental surface 1 to 60 minutes, or 1 to 30 minutes, or 1 to 5 minutes.

In one embodiment, the dental surface is in need of such treatment. Therefore the invention includes in addition to the steps of any method described herein a step of identifying a subject suffering fluorosis, dental caries, dentinal hypersensitivity or dental calculus, a white spot lesion; a fluorotic lesion; a caries lesion; or a lesion caused by tooth erosion, or dental plaque or gingivitis or periodontitis.

The present invention provides a composition for mineralizing a dental surface or sub-surface that is also capable of reducing plaque, gingivitis and periodontitis comprising (a) a composition including a stannous compound and stabilized ACP or ACFP, or (b) a stannous-associated stabilized ACP or ACFP.

In a further aspect, there is provided a method of treating or preventing one or more of each of dental caries, tooth decay, dental erosion and fluorosis, comprising the steps of administering (a) a composition including a stannous compound and stabilized ACP or ACFP, or (b) a stannous-associated stabilized ACP or ACFP, thereby treating or preventing one or more of each of dental caries, tooth decay, dental erosion and fluorosis. Topical administration of the complex is preferred. The method preferably includes the administration of the complex in a formulation as described above.

The present invention also provides a composition containing a stannous-associated stabilized ACP or ACFP. Preferably, the composition further includes a pharmaceutically acceptable carrier, diluent or excipient.

In a preferred embodiment, the phosphopeptide stabilised amorphous calcium phosphate (ACP) or amorphous calcium fluoride phosphate (ACFP) complex in the composition has tightly bound and loosely bound calcium, wherein the bound calcium in the complex is less than the tightly bound calcium in an ACP or ACFP complex formed at a pH of 7.0. Optionally, the ACP or ACFP is predominantly in a basic form.

In another preferred embodiment, the calcium ion content of the stabilised ACP or ACFP complex in the composition is in the range of about 30 to 100 moles of calcium per mole of PP. More preferably, the calcium ion content is in the range of about 30 to about 50 moles of calcium per mole of PP.

In any embodiment as described herein, the ACP and/or ACFP in the composition can be in the form of a casein phosphopeptide stabilized ACP and/or ACFP complex.

The invention also relates to a kit for the treatment or prevention of one or more of dental caries, fluorosis, dental hypersensitivity and dental erosion including:
(a) a compound capable of increasing or maintaining the pH of a solution, and
(b) a composition including a stannous compound and stabilized ACP or ACFP, or
(c) a stannous-associated stabilized ACP or ACFP.

Preferably, the stannous-associated stabilized ACP or ACFP is in a pharmaceutically acceptable carrier. Desirably, the kit further includes instructions for their use for the mineralization of a dental surface in a patent in need of such treatment. The instructions may describe the use of the kit to treat or prevent one or more of each of dental caries, tooth decay, dental erosion, dental hypersensitivity and fluorosis. In one embodiment, the agent and the complex are present in suitable amounts for treatment of a patient.

The composition or kit of the invention may further include a source of fluoride ions. The fluoride ions may be from any suitable source. A source of fluoride ions may include free fluoride ions or fluoride salts. Examples of sources of fluoride ions include, but are not limited to the following: sodium fluoride, sodium monofluorophosphate, stannous fluoride, sodium silicofluoride and amine fluoride. These may be provided in solution (typically an aqueous solution), or a suspension.

DETAILED DESCRIPTION OF THE EMBODIMENTS

Figure 1:
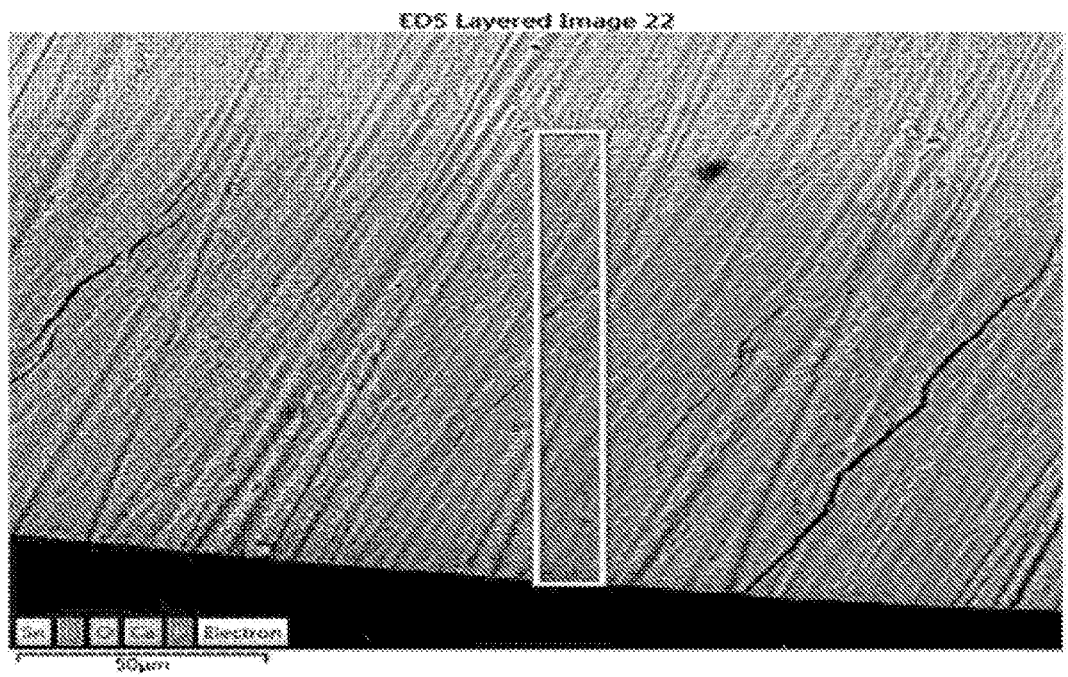
FIG. 1: Representative SEM images of enamel subsurface lesions before (A) and after (B) treatment with stabilized $SnF_2$/ACP also demonstrating the surface layer.
Figure 1:
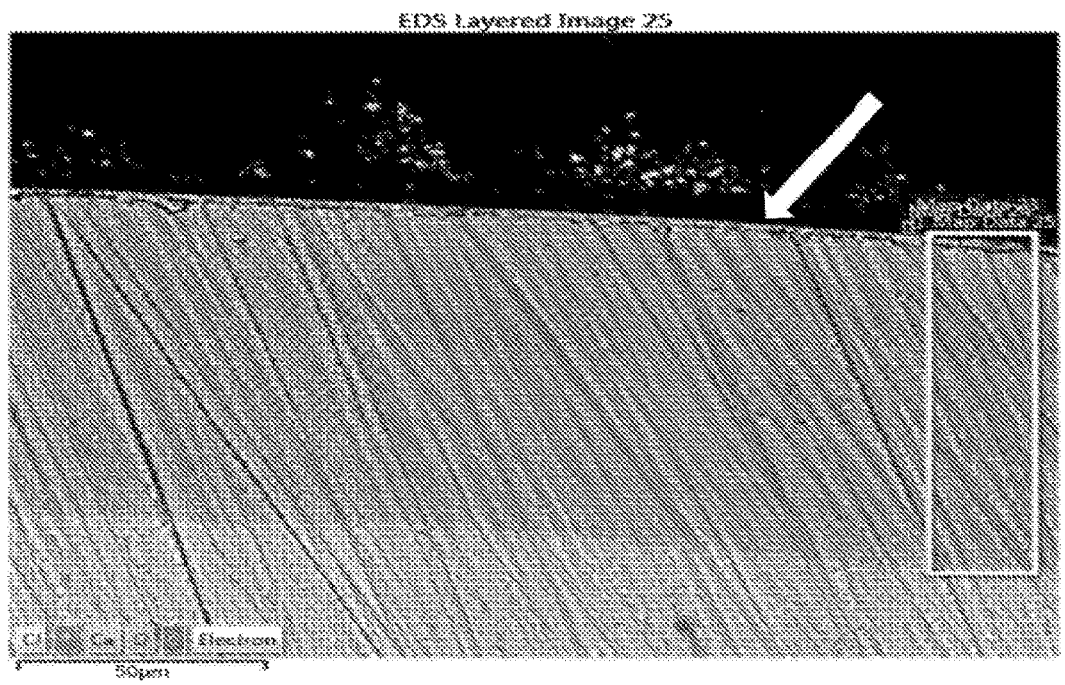

It will be understood that the invention disclosed and defined in this specification extends to all alternative combinations of two or more of the individual features mentioned or evident from the text or drawings. All of these different combinations constitute various alternative aspects of the invention.

Further aspects of the present invention and further embodiments of the aspects described in the preceding paragraphs will become apparent from the following description, given by way of example and with reference to the accompanying drawings.

Reference will now be made in detail to certain embodiments of the invention. While the invention will be described in conjunction with the embodiments, it will be understood that the intention is not to limit the invention to those embodiments. On the contrary, the invention is intended to cover all alternatives, modifications, and equivalents, which may be included within the scope of the present invention as defined by the claims.

One skilled in the art will recognize many methods and materials similar or equivalent to those described herein, which could be used in the practice of the present invention. The present invention is in no way limited to the methods and materials described.

All of the patents and publications referred to herein are incorporated by reference in their entirety.

For purposes of interpreting this specification, terms used in the singular will also include the plural and vice versa.

As used herein, except where the context requires otherwise, the term "comprise" and variations of the term, such as "comprising", "comprises" and "comprised", are not intended to exclude further additives, components, integers or steps. As used herein, except where the context requires otherwise, "comprise" and "include" can be used interchangeably.

The present invention is based on the finding that casein phosphopeptides can stabilize a stannous compound, such as $SnF_2$, in an aqueous environment and in the presence of stabilized amorphous calcium phosphate (ACP) and stabilized amorphous calcium fluoride phosphate (ACFP) these formulations are superior to other forms of fluoride and stabilized ACP or ACFP in remineralizing enamel subsurface lesions. Mineralization of dental surfaces can be significantly enhanced by providing a stannous compound during the process of mineralization by stabilized ACP and/or stabilized ACFP. In particular, it has been found that the mineralization of enamel by stabilized soluble forms of stannous-associated ACP complexes and stannous-associated ACFP complexes is enhanced compared with stabilized ACP and fluoride without associated stannous.

The stannous ion in the presence of stabilized ACP and/or stabilized ACFP can produce a protective surface layer on the enamel/dentine to help prevent dental caries, dentinal hypersensitivity, dental plaque and periodontal disease. The layer which includes stannous ions and stabilized ACP and/or stabilized ACFP can provide a reservoir for calcium, phosphate, and fluoride for mineralization of the tooth surface or subsurface. These formulations have been designated stannous-associated stabilized ACP and stannous-associated stabilized ACFP.

Without being bound by any theory or mode of action it is believed that the stannous ions are stabilized by the presence of the phosphopeptides, particularly casein phosphopeptides. Therefore, it is believed that the phosphopeptides deliver stannous and fluoride ions together with the calcium and phosphate ions to promote remineralization. Remineralization may be a result of formation of calcium and stannous fluorapatite. It is also believed that the stannous ions cross-link the phosphopeptide stabilized ACP or stabilized ACFP at the tooth surface to form a layer that can protect the tooth surface from demineralization. The presence of the stannous in the surface layer would render it hard and resistant to degradation due to normal wear and tear or other processes such as erosion. A further advantage of the invention is that the stannous ions may assist to kill oral bacteria that produce acid and other metabolic products which promote demineralization.

Stannous is known to form precipitates with hydroxide ions and phosphate ions thereby reducing the bioavailabiltiy and activity of the stannous ion. The resulting promotion of stabilized-ACP/stabilized-ACFP driven remineralization by stannous ions is surprising as it would be expected that the hydroxide ions (eg $OH^-$) and phosphate ions (eg $PO_4^{3-}$) provided by the stabilized-ACP or stabilized-ACFP would cause precipitation of the stannous to stannous hydroxide and stannous phosphate, thereby severely decreasing any activity of the stannous containing compound. Further, it would be expected that formation of a precipitate of stannous ions with hydroxide ions would not only reduce the bioavailability of the stannous ions but also remove hydroxide ions from the environment thereby reducing the pH. A reduction in pH would promote demineralization and hinder mineralization.

The present invention provides stannous-associated stabilized ACP or ACFP complexes and methods of mineralizing a dental surface or sub-surface comprising contacting the dental surface or subsurface with a stannous-associated stabilized ACP or ACFP complexes. A dental subsurface is typically a hypomineralized lesion such that the stannous-associated stabilized ACP or ACFP complexes contacted to the dental surface migrate through any surface layer, i.e. pellicle and/or plaque, through the porous dental surface to the region requiring mineralization. These stannous-associated stabilized ACP or ACFP complexes also generate a protective surface layer on the enamel/dentine to help prevent dental caries, dentinal hypersensitivity, dental plaque and periodontal disease The dental surface is preferably dental enamel or dentine. The dental surface may be a lesion in the enamel, such as a lesion caused by caries, dental erosion or fluorosis.

In one aspect the invention provides, a stannous-associated stabilized amorphous calcium phosphate (ACP) or stannous-associated amorphous calcium fluoride phosphate (ACFP). The stannous may be bound to the stabilized amorphous calcium phosphate (ACP) and/or amorphous calcium fluoride phosphate (ACFP) as determined using the experimental protocol in Example 2. In one embodiment, the stannous-associated stabilized ACP or stannous-associated stabilized ACFP are produced by a method as described herein, including but not limited to, the method described in Example 1.

The stannous is present in the stannous-associated stabilized amorphous calcium phosphate (ACP) or stannous-associated amorphous calcium fluoride phosphate (ACFP) complex by binding to or being incorporated in the complex. This complex associated stannous, wherein the stannous is bound to or incorporated in the complex, can be determined using filtration and atomic absorption spectrophotometry. Tightly associated complexed stannous is measured as the difference between total stannous less loosely-bound stannous. To determine the total stannous (both tightly & loosely bound) present in a solution of stannous-associated complexes, a solution containing the complexes was taken and placed into HNO3 and incubated at room temperature with constant slow end over end mixing for 24 hrs. The mixture can then be centrifuged at about 1000 g, preferably for 15 minutes at room temperature. The supernatant when analysed for stannous ion content, preferably by atomic absorption spectrophotometry (AAS), will provide the value for the total stannous present (whether that be bound/associated with the complex or free in solution). The level of loosely-bound stannous in the solution can then be determined by taking a sample of a solution of stannous-associated complexes, placing it in a centricon with a 1000 MWCO filter and centrifuging at about 3000 g, preferably for 1 hour at room temperature, to produce enough filtrate (<10% of total sample to not affect equilibrium) for analysis by AAS. The filtrates contain loosely-bound stannous ions. Tightly CPP-bound (colloidal retentate) stannous ions can then be calculated from the difference between total and loosely-bound stannous ions. 'Loosely-bound' stannous is stannous that is separable from a complex only by a method such as centrifugation as described above. The loosely-bound stannous is still associated with the complexes but is more easily dissociable than tightly-bound stannous ions by the less stringent conditions explained above.

In one embodiment, the stannous-associated stabilized amorphous calcium phosphate (ACP) or stannous-associated amorphous calcium fluoride phosphate (ACFP) complex including stannous that cannot be separated from the complex by centrifugation at about 3000 g, preferably for 1 hour at room temperature.

In a further aspect of the present invention there is provided a method of mineralizing a dental surface comprising providing (a) a composition including a stannous compound and stabilized ACP or ACFP, or (b) a stannous-associated stabilized ACP or ACFP. In a preferred embodiment the dental surface is enamel.

In a further aspect of the present invention there is provided a method for treating fluorosis comprising contacting a fluorotic lesion in tooth enamel with (a) a composition including a stannous compound and stabilized ACP or ACFP, or (b) a stannous-associated stabilized ACP or ACFP.

In a further aspect of the present invention there is provided a method for treating dental caries comprising contacting a caries lesion in tooth enamel with (a) a composition including a stannous compound and stabilized ACP or ACFP, or (b) a stannous-associated stabilized ACP or ACFP.

In a further aspect of the present invention there is provided a method for treating dental erosion comprising contacting a lesion in tooth enamel caused by erosion with (a) a composition including a stannous compound and stabilized ACP or ACFP, or (b) a stannous-associated stabilized ACP or ACFP.

In a further aspect of the present invention there is provided a method for inhibiting the progression of dental erosion comprising contacting a surface exhibiting erosion with (a) a composition including a stannous compound and stabilized ACP or ACFP, or (b) a stannous-associated stabilized ACP or ACFP, thereby forming a surface layer that inhibits the progression of dental erosion.

In a further aspect of the present invention there is provided a method for reducing dentinal hypersensitivity on exposed dentine comprising contacting the dentine with (a) a composition including a stannous compound and stabilized ACP or ACFP, or (b) a stannous-associated stabilized ACP or ACFP.

In a further aspect of the present invention there is provided a method for remineralizing a lesion in tooth enamel comprising contacting the lesion with (a) a composition including a stannous compound and stabilized ACP or ACFP, or (b) a stannous-associated stabilized ACP or ACFP.

In a further aspect of the present invention there is provided a method of increasing the remineralization efficacy of a composition having stabilized ACP and/or ACFP the method including the step of adding a stannous compound to the composition. Preferably, the stannous compound is added to the composition when it is in aqueous state, such as during manufacture.

Preferably the stannous-associated stabilized ACP or ACFP is stabilized by a phosphopeptide. In a preferred embodiment the phosphopeptide is a casein phosphopeptide. Preferably, the ACP or ACFP is in the form of a casein phosphopeptide stabilized ACP or ACFP complex.

In any aspect or embodiments as described herein, the stabilized ACP and/or ACFP may be in a formulation with additional calcium phosphate. Typically, the formulation includes a PP stabilized ACP and/or ACFP complex together with at least an equal amount by weight of calcium phosphate.

A composition including a stannous compound and stabilized ACP or ACFP may be contacted with the dental surface for a period of about 1 to 60 minutes, or for about 1 to 30 minutes. In one embodiment, the composition including a stannous compound and stabilized ACP or ACFP is contacted with the dental surface for about 20 minutes. An example of how this is achieved is formulating stannous compound and stabilized ACP or ACFP into an oral composition, such as a paste, and then contacting or applying the composition to the dental surface. The oral composition, such as a paste, has sufficient viscosity to be retained on the tooth for the required time period.

Preferably a composition including a stannous compound and stabilized ACP or ACFP is contacted with the dental surface for a period of about 1 minute to 2 hours, or 5 minutes to 60 minutes or about 10 minutes. The a composition including a stannous compound and stabilized ACP/ACFP may be repeatedly applied to the dental surface over a period of 1 day to several months.

A stannous-associated stabilized ACP or ACFP may be contacted with the dental surface for a period of about 1 to 60 minutes, or for about 1 to 30 minutes. In one embodiment, the stannous-associated stabilized ACP or ACFP is contacted with the dental surface for about 20 minutes. An example of how this is achieved is formulating the stannous-associated stabilized ACP or ACFP into an oral composition, such as a paste, and then contacting or applying the composition to the dental surface. The oral composition, such as a paste, has sufficient viscosity to be retained on the tooth for the required time period.

Preferably a stannous-associated stabilized ACP or ACFP is contacted with the dental surface for a period of about 1 minute to 2 hours, or 5 minutes to 60 minutes or about 10 minutes. The stannous-associated stabilized ACP or ACFP may be repeatedly applied to the dental surface over a period of 1 day to several months.

In one embodiment, the dental surface is in need of such treatment. Therefore, in another aspect, the invention includes in addition to the steps of any method described herein a step of identifying a subject suffering fluorosis, dental caries, dentinal hypersensitivity or dental calculus, a white spot lesion; a fluorotic lesion; a caries lesion; or a lesion caused by tooth erosion, dental plaque, gingivitis or periodontitis.

The present invention provides (a) a composition including a stannous compound and stabilized ACP or ACFP, or (b) a stannous-associated stabilized ACP or ACFP for use in mineralizing a dental surface or sub-surface and reducing the viability of bacteria on that dental surface.

In any method of the invention, the stannous compound and stabilized ACP or ACFP are applied to the dental surface sequentially or concurrently. In any embodiment, the stannous compound is added prior to the stabilized ACP or ACFP. In any embodiment, the stannous compound is added after the stabilized ACP or ACFP.

A stannous-associated stabilized ACP or ACFP complex as referred to herein include a stannous-associated stabilized-ACP or ACFP complex formed at a pH of below 7.0. Preferably the complex is formed at a pH in the range of about 5.0 up to but below 7.0. More preferably the complex is formed at a pH range of about 4.0 to 6.5, or 5.0 to about 6.0. In one embodiment, the pH during formation is maintained at pH 6.5 or below. In a preferred embodiment, the complex is formed at a pH of about 5.5. Preferably, the ACP or ACFP in the complex is predominantly in a basic form. The stannous-associated stabilized ACP or ACFP complex when produced on an industrial scale is produced in a bulk solution that has a pH greater than about 7.0, preferably about 9.0, however the local pH at formation of the complexes is below about 7.0, preferably about 4.0 to 6.5, preferably about 5.5.

When stannous-associated stabilized ACP or ACFP, or stabilized ACP or ACFP, is produced in the laboratory, in smaller quantities than commercial production the pH of the entire solution may be maintained at a given pH, i.e. if the CPP-ACP was prepared at pH 5.5, then the entire solution during CPP-ACP formation was maintained at pH 5.5.

However, it may be neither necessary nor desirable to reduce the pH of the entire bulk solution in commercial manufacture to 5.5 as the only part of the bulk solution required to have the acidic pH is where the complexes are forming and the bulk solution can have, and does have, localised fluctuations in pH. The pH fluctuations arise particularly from protons provided by the phosphate compound, for example dihydrogen phosphate, as it is added and the protons liberated from acidic phosphate ions when they convert into the basic form, $PO_4^{3-}$. Therefore, while the overall pH of the bulk solution may be at above 7.0, for example about pH 9, the localised pH at which the CPP-ACP is formed is lower, typically below 7.0 or 6.5, preferably about 4.0 to 6.5, more preferably about 5.5. These fluctuations are localised due to the size of the bulk solution.

One method for forming a stannous-associated stabilized ACP of the invention is a method comprising the steps of:
(i) obtaining a solution comprising at least one phosphopeptide and;
(ii) admixing solutions comprising calcium ions, phosphate ions and hydroxide ions, while maintaining the pH at about 7.0 or below; and
(iii) admixing a stannous compound;
or
(i) providing a solution of stabilized ACP; and
(ii) admixing a stannous compound.

One method for forming a stannous-associated stabilised ACFP is a method comprising the steps of:
(i) obtaining a solution comprising at least one phosphopeptide and;
(ii) admixing solutions comprising calcium ions, phosphate ions, hydroxide ions and fluoride ions, while maintaining the pH at about 7.0 or below; and
(iii) admixing a stannous compound;
or
(i) providing a solution of stabilized ACFP; and
(ii) admixing a stannous compound.

The hydroxide ions may be titrated into the solution to maintain the phosphopeptide solution at an essentially constant pH. The calcium and phosphate ions may be titrated into the phosphopeptide solution with constant mixing and at a rate that avoids the formation of a calcium phosphate precipitate in the phosphopeptide solution.

A stannous-associated stabilized ACP may be produced by a method comprising the step of admixing CPP-ACP and a stannous compound in an aqueous solution, while maintaining the pH at about 6.5 or below.

A stannous-associated stabilized ACFP may be produced by a method comprising the step of admixing CPP-ACFP and a stannous compound in an aqueous solution, while maintaining the pH at about 6.5 or below.

A stannous-associated stabilized ACP may be produced by a method comprising the steps of:
(i) obtaining a solution comprising CPP-ACP; and;
(ii) admixing a stannous compound, while maintaining the pH at about 6.5 or below.

A stannous stabilised ACFP may be produced by a method comprising the steps of:
(i) obtaining a solution comprising CPP-ACFP; and;
(ii) admixing a stannous compound, while maintaining the pH at about 6.5 or below.

Preferably, the stannous compound is stannous fluoride. Optionally, the methods of producing stannous-associated stabilized ACP or stannous-associated stabilized ACFP further comprise admixing sodium fluoride in step (ii).

Preferably the pH is maintained with an acid, such as HCl.

Preferably the solution comprising CPP-ACP or CPP-ACFP is prepared by adding CPP-ACP or CPP-ACFP to distilled or deionised water.

A stannous-associated stabilized amorphous calcium phosphate (ACP) and/or amorphous calcium fluoride phosphate (ACFP) complex may be formed by mixing stabilized stabilized amorphous calcium phosphate (ACP) and/or amorphous calcium fluoride phosphate (ACFP) complex with stannous fluoride.

Figure 2:
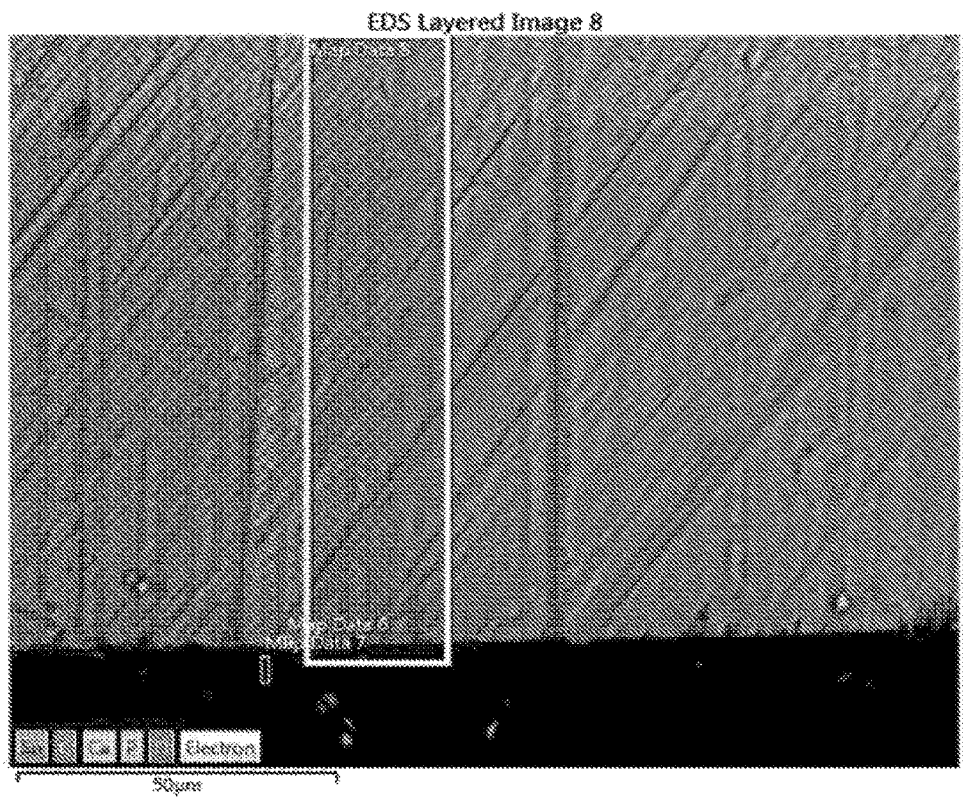
FIG. 2: Representative SEM images of enamel subsurface lesions before (A) and after (B) treatment with stabilized NaF/ACP [Note no formation of a novel surface layer].
Figure 2:
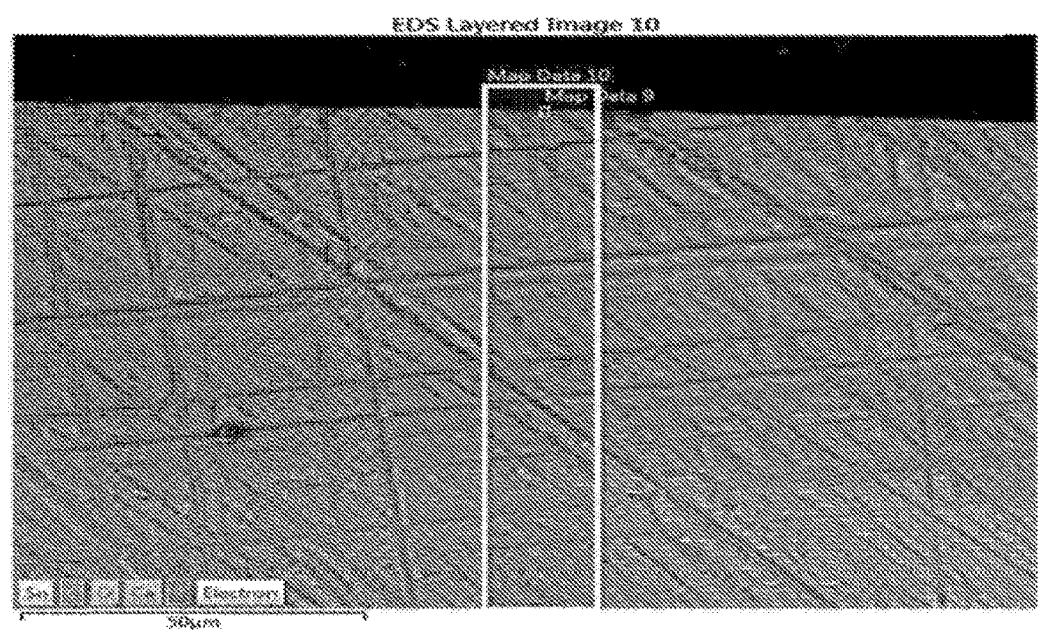

A stabilized-ACP or ACFP complex as described in the current specification may be the "closed" complexes are shown in FIG. 2 of Cross et al., 2007.

A stabilized-ACP or ACFP complex as referred to herein include a stabilized-ACP or ACFP complex as described in PCT/AU2005/001781 the contents of which are incorporated by reference.

In a preferred embodiment, the phosphopeptide stabilised amorphous calcium phosphate (ACP) or amorphous calcium fluoride phosphate (ACFP) complex has tightly bound and loosely bound calcium, wherein the bound calcium in the complex is less than the tightly bound calcium in an ACP or ACFP complex formed at a pH of 7.0. Optionally, the ACP or ACFP is predominantly in a basic form.

A stabilized-ACP or ACFP complex as referred to herein include a stabilized-ACP or ACFP complex formed at a pH of below 7.0. Preferably the complex is formed at a pH in the range of about 5.0 up to but below 7.0. More preferably the complex is formed at a pH range of about 5.0 to about 6.0. In a preferred embodiment, the complex is formed at a pH of about 5.5. Preferably, the ACP or ACFP in the complex is predominantly in a basic form.

A stabilized-ACP may be produced by a method comprising the steps of:
(i) obtaining a solution comprising at least one phosphopeptide and;
(ii) admixing solutions comprising calcium ions, phosphate ions and hydroxide ions, while maintaining the pH at about 7.0 or below.

A stabilised ACFP may be produced by a method comprising the steps of:
(i) obtaining a solution comprising at least one phosphopeptide and;

(ii) admixing solutions comprising calcium ions, phosphate ions, hydroxide ions and fluoride ions, while maintaining the pH at about 7.0 or below.

A phosphopeptide stabilised amorphous calcium phosphate (ACP) or amorphous calcium fluoride phosphate (ACFP) complex may also include wherein the ACP in the complex has tightly bound and loosely calcium, wherein the tightly bound calcium in the complex is less than the tightly bound calcium in an ACP or ACFP complex formed at a pH of 7.0 and the ACP or ACFP is predominantly in a basic form, obtainable or obtained by a method comprising:
a) admixing a first solution comprising calcium ions, a second solution comprising phosphate ions, and optionally a third solution comprising fluoride ions, to a solution comprising phosphopeptides and a solvent with a pH of from about 5 up to but below 7; and
b) maintaining the pH of the solution at about 5.0 up to but below 7.0 during the admixing by adding hydroxide ions.

"Tightly" and "loosely" bound calcium and phosphate in ACP or ACFP can be determined using analytical ultrafiltration. Briefly, the solution of phosphopeptide, calcium, phosphate and optionally fluoride admixed while maintaining the pH at about 7.0 or below can be first filtered through a 0.1 micron filter to remove free calcium and phosphate that is not associated with the complexes. This free calcium and phosphate is present in the filtrate and discarded. Any free calcium or phosphate that is not associated in any way with the complexes would not be bioavailable, i.e. delivered by the phosphopeptide to the tooth. The retentate from the 0.1 micron filtration can be further analyzed by centrifugation through a 3000 mw cutoff filter at 1,000 g for 15 min. The resulting filtrate contains calcium and phosphate that is loosely bound or associated with the complexes. At this centrifugal force calcium and phosphate that is not tightly bound to the complexes are released and move to into the filtrate. The Ca and Pi that is tightly bound in the complexes is retained in the retentate. The amount of tightly bound Ca and Pi in the retentate can then be determined by subtracting the amount of Ca and Pi in the filtrate from the total amount of Ca and Pi in the retentate of the 0.1 micron filtration.

A stabilized-ACP or ACFP complex as referred to herein include a stabilized-ACP or ACFP complex as described in PCT/AU2006/000885 the contents of which are incorporated by reference.

A "superloaded" phosphopeptide or phosphoprotein (PP) stabilized-amorphous calcium phosphate (ACP) or amorphous calcium fluoride phosphate (ACFP) complex. The complex may be formed at any pH (eg 3-10). Preferably the phosphopeptide includes the sequence -A-B-C-, where A is a phosphoamino acid, preferably phosphoserine, B is any amino acid including a phosphoamino acid and C is glutamic acid, aspartic acid or a phosphoamino acid. The phosphoamino acid may be phosphoserine. The PP is superloaded with calcium and phosphate ions. The calcium ions may be in the range 30-1000 mol Ca per mole of PP, or in the range of 30-100 or 30-50 mole Ca per mole of PP. In another embodiment, the mol Ca per mol of PP is at least 25, 30, 35, 40, 45 or 50.

The phosphopeptide or phosphoprotein (PP) stabilized amorphous calcium phosphate or amorphous calcium fluoride phosphate complex may have a calcium ion content greater than about 30 moles of calcium per mole of PP. In a preferred embodiment, the calcium ion content is in the range of about 30 to 100 moles of calcium per mole of PP. More preferably, the calcium ion content is in the range of about 30 to about 50 moles of calcium per mole of PP.

The phosphopeptide or phosphoprotein (PP) stabilized-amorphous calcium phosphate (ACP) or amorphous calcium fluoride phosphate (ACFP) complex may be produced by a method comprising the steps of:
(i) obtaining solutions comprising calcium, inorganic phosphate and fluoride (optional); and
(ii) admixing (i) with a solution comprising PP-ACP.

In a preferred embodiment, the PP is casein phosphopeptide (CPP).

The PP stabilized ACP and/or ACFP complex may further include at least an equal amount by weight of calcium phosphate. Preferably the calcium phosphate is $CaHPO_4$. Preferably, the calcium phosphate (e.g. $CaHPO_4$) is dry blended with the PP stabilized ACP and/or ACFP complex. In a preferred embodiment, the PP-ACP and/or PP-ACFP complex:calcium phosphate ratio is about 1:1-50. more preferably about 1: 1-25, more preferably about 1:5-15. In one embodiment, the PP-ACP and/or PP-ACFP complex:calcium phosphate ratio is about 1:10.

The oral care formulation that includes a phosphopeptide or phosphoprotein (PP) stabilized amorphous calcium phosphate (ACP) and/or amorphous calcium fluoride phosphate (ACFP) complex having a calcium ion content greater than about 30 moles of calcium per mole of PP when used in the oral cavity may be produced by a method including the steps of:
(i) obtaining a powder including a PP-ACP and/or PP-ACFP complex;
(ii) dry blending with an effective amount of calcium phosphate; and
(iii) formulating the dry blended PP-ACP and/or PP-ACFP and calcium phosphate mixture into an oral care formulation.

Preferably, the form of calcium phosphate for dry blending is any soluble calcium phosphate including, but not limited to, $CaHPO_4$, $Ca_2HPO_4$ and calcium lactate.

The present invention also provides a method of mineralizing a dental surface or sub-surface including the steps of:
(i) contacting the dental surface with a protein disrupting agent, and
(ii) contacting the dental surface with (a) a composition including a stannous compound and stabilized ACP or ACFP, or (b) a stannous-associated stabilized ACP or ACFP.

The dental surface is preferably dental enamel. In one embodiment the dental surface is a lesion in the enamel, such as a lesion caused by caries, dental erosion or fluorosis. Any suitable protein disrupting agent can be used in the method of the present invention. The agent is required to reduce the proteinaceous barrier formed over the surface to be treated, such as the pellicle over teeth. Examples of suitable agents include bleach, detergent, chaotropic agents such as urea, high phosphate concentrations, cocktails of proteases (e.g. endopeptidases, proteinases and exopeptidases) and any other protein solubilizing, disrupting or hydrolysing agent. Examples of suitable bleaches include sodium hypochlorite (NaOCl), and cabamide peroxide bleaches. In a preferred embodiment, the bleach is an alkaline bleach. In a further preferred embodiment the alkaline bleach is NaOCl. The protein disrupting agent acts to solubilize and partially or wholly remove proteins from the dental surface, particularly proteins of the pellicle.

A composition as described herein may further include free fluoride ions. The fluoride ions may be from any suitable source. A source of fluoride ions may include free fluoride ions or fluoride salts. Examples of sources of fluoride ions include, but are not limited to the following:

sodium fluoride, sodium monofluorophosphate, stannous fluoride, sodium silicofluoride and amine fluoride. These may be provided in solution (typically an aqueous solution), or a suspension.

The fluoride ions are preferably present in the composition in an amount greater than 1 ppm. More preferably, the amount is more than 3 ppm. In another embodiment, it is preferably more than 10 ppm. In typical embodiments described below, the amount may be several hundred or thousand ppm. The fluoride content is typically measured as a ppm in oral compositions in the manner commonly used in the art. Where the fluoride is provided from a source with the stabilized ACP, the ppm refers to the concentration of the fluoride in that source, typically a solution or suspension of bioavailable fluoride.

"Phosphopeptide" in the context of the description of this invention means an amino acid sequence in which at least one amino acid is phosphorylated. Preferably, the phosphopeptide includes one or more of the amino acid sequence -A-B-C-, where A is a phosphoamino residue, B is any amino acyl residue including a phosphoamino residue and C is selected from a glutamyl, aspartyl or phosphoamino residue. Any of the phosphoamino residues may independently be a phosphoseryl residue. B is desirably a residue the side-chain of which is neither relatively large nor hydrophobic. It may be Gly, Ala, Val, Met, Leu, Ile, Ser, Thr, Cys, Asp, Glu, Asn, Gln or Lys.

In another embodiment, at least two of the phosphoamino acids in the sequence are preferably contiguous. Preferably the phosphopeptide includes the sequence A-B-C-D-E, where A, B, C, D and E are independently phosphoserine, phosphothreonine, phosphotyrosine, phosphohistidine, glutamic acid or aspartic acid, and at least two, preferably three, of the A, B, C, D and E are a phosphoamino acid. In a preferred embodiment, the phosphoamino acid residues are phosphoserine, most preferably three contiguous phosphoserine residues. It is also preferred that D and E are independently glutamic or aspartic acid.

In one embodiment, the ACP or ACFP is stabilized by a casein phosphopeptide (CPP), which is in the form of intact casein or fragment of the casein, and the complex formed preferably has the formula [CPP(ACP)$_8$]$_n$ or [(CPP)(ACFP)$_8$]$_n$ where n is equal to or greater than 1, for example 6. The complex formed may be a colloidal complex, where the core particles aggregate to form large (eg 100 nm) colloidal particles suspended in water. Thus, the PP can be a casein protein or a phosphopeptide.

The PP may be from any source; it may be present in the context of a larger polypeptide, including a full length casein polypeptide, or it may be isolated by tryptic or other enzymatic or chemical digestion of casein, or other phosphoamino acid rich proteins such as phosphitin, or by chemical or recombinant synthesis, provided that it comprises the sequence -A-B-C- or A-B-C-D-E as described above. The sequence flanking this core sequence may be any sequence. However, those flanking sequences in $\alpha_{s1}$(59-79) [1], $\beta$(1-25) [2], $\alpha_{s2}$(46-70) [3] and $\alpha_{s2}$(1-21) [4] are preferred. The flanking sequences may optionally be modified by deletion, addition or conservative substitution of one or more residues. The amino acid composition and sequence of the flanking region are not critical.

Examples of conservative substitutions are shown in Table 1 below.

TABLE 1

| Original Residue | Exemplary Conservative Substitution | Preferred Conservative Substitution |
|---|---|---|
| Ala | Val, Leu, Ile | Val |
| Asn | Gln Lys His Phe | Gln |
| Gln | Asn | Asn |
| Gly | Pro | Pro |
| Ile | Leu, Val, Met, Ala, Phe | Leu |
| Leu | Ile, Val, Met, Ala, Phe | Ile |
| Lys | Arg, Gln, Asn | Arg |
| Phe | Leu, Val, Ile, Ala | Leu |
| Pro | Gly | Gly |
| Ser | Thr | Thr |
| Val | Ile, Leu, Met, Phe, Ala | Leu |
| Asp | Gu | Glu |
| Thr | Ser | Ser |
| Trp | Tyr | Tyr |
| Tyr | Trp Phe Thr Ser | Phe |

The flanking sequences may also include non-naturally occurring amino acid residues. Commonly encountered amino acids which are not encoded by the genetic code, include:
2-amino adipic acid (Aad) for Glu and Asp;
2-aminopimelic acid (Apm) for Glu and Asp;
2-aminobutyric (Abu) acid for Met, Leu, and other aliphatic amino acids;
2-aminoheptanoic acid (Ahe) for Met, Leu and other aliphatic amino acids;
2-aminoisobutyric acid (Aib) for Gly;
cyclohexylalanine (Cha) for Val, and Leu and Ile;
homoarginine (Har) for Arg and Lys;
2, 3-diaminopropionic acid (Dpr) for Lys, Arg and His;
N-ethylglycine (EtGly) for Gly, Pro, and Ala;
N-ethylasparigine (EtAsn) for Asn, and Gln;
Hydroxyllysine (Hyl) for Lys;
allohydroxyllysine (AHyl) for Lys;
3-(and 4) hydroxyproline (3Hyp, 4Hyp) for Pro, Ser, and Thr;
alloisoleucine (AIle) for Ile, Leu, and Val;
ρ-amidinophenylalanine for Ala;
N-methylglycine (MeGly, sarcosine) for Gly, Pro, Ala.
N-methylisoleucine (MeIle) for Ile;
Norvaline (Nva) for Met and other aliphatic amino acids;
Norleucine (Nle) for Met and other aliphatic amino acids;
Ornithine (Orn) for Lys, Arg and His;
Citrulline (Cit) and methionine sulfoxide (MSO) for Thr, Asn and Gln;
N-methylphenylalanine (MePhe), trimethylphenylalanine, halo (F, Cl, Br and I) phenylalanine, triflourylphenylalanine, for Phe.

In one embodiment, the PP is one or more phosphopeptides selected from the group consisting of $\alpha_{s1}$(59-79) [1], $\beta$(1-25) [2], $\alpha_{s2}$(46-70) [3] and $\alpha_{s2}$(1-21) [4]:

[1]
Gln[59]-Met-Glu-Ala-Glu-Ser(P)-Ile-Ser(P)-Ser(P)-Ser(P)-Glu-Glu-Ile-Val-Pro-Asn-Ser(P)-Val-Glu-Gln-Lys[79] $\alpha_{s1}$(59-79)

[2]
Arg[1]-Glu-Leu-Glu-Glu-Leu-Asn-Val-Pro-Gly-Glu-Ile-Val-Glu-Ser(P)-Leu-Ser(P)-Ser(P)-Ser(P)-Glu-Glu-Ser-Ile-Thr-Arg[25] $\beta$(1-25)

[3]
Asn[46]-Ala-Asn-Glu-Glu-Glu-Tyr-Ser-Ile-Gly-Ser(P)-Ser(P)-Ser(P)-Glu-Glu-Ser(P)-Ala-Glu-Val-Ala-Thr-Glu-Glu-Val-Lys[70] $\alpha_{s2}$(46-70)

-continued

[4]
Lys¹-Asn-Thr-Met-Glu-His-Val-Ser(P)-Ser(P)-Ser(P)-Glu-Glu-Ser-Ile-Ile-Ser(P)-Gln-Glu-Thr-Tyr-Lys²¹
$\alpha_{s2}(1-21)$.

In another embodiment of the invention, the stannous-associated stabilized ACP and/or stannous-associated stabilized ACFP complex is incorporated into oral compositions such as toothpaste, mouth washes or formulations for the mouth to aid in the prevention and/or treatment of dental caries, tooth decay, dental erosion or fluorosis, dentinal hypersensitivity, dental plaque, gingivitis or periodontitis. The oral compositions comprising an amount of stannous-associated stabilized ACP and/or ACFP sufficient to form a layer on a dental surface, preferably, the layer has a calcium:phosphate ratio equivalent to normal apatite, for example the ratio is about 2:1. The layer may contain an amount of calcium that is about 20 wt %. Preferably, the layer may exhibit about an elemental analysis of any one of the elements, such as calcium, phosphate, fluoride, carbon and/or stannous, as shown in any one of Table 3 or 4. The stannous-associated stabilized ACP and/or ACFP complexes may comprise 0.01-50% by weight of the composition, preferably 1.0-50%. For oral compositions, it is preferred that the amount of the stannous-associated stabilized ACP or ACFP complexes administered is 0.01-50% by weight, preferably 1.0%-50% by weight of the composition. In a particularly preferred embodiment, the oral composition of the present invention contains about 2% stannous-associated stabilized ACP or ACFP complexes or a mixture of both. The oral composition of this invention which contains the above-mentioned agents may be prepared and used in various forms applicable to the mouth such as dentifrice including toothpastes, toothpowders and liquid dentifrices, mouthwashes, mouthrinses, mouth sprays, varnish, dental cement, troches, chewing gums, dental pastes, gingival massage creams, gargle tablets, dairy products and other foodstuffs. The oral composition according to this invention may further include additional well known ingredients depending on the type and form of a particular oral composition. Certain compositions of the invention such as toothpastes, toothpowders and liquid dentifrices, mouthwashes, mouthrinses and mouth sprays have relatively low viscosity and have a remineralizing effect without significant residence time in the oral cavity.

In certain preferred forms of the invention an oral composition may be substantially liquid in character, such as a mouthwash, rinse or spray. In such a preparation the vehicle is typically a water-alcohol mixture desirably including a humectant as described below. Generally, the weight ratio of water to alcohol is in the range of from about 1:1 to about 20:1. The total amount of water-alcohol mixture in this type of preparation is typically in the range of from about 70 to about 99.9% by weight of the preparation. The alcohol is typically ethanol or isopropanol. Ethanol is preferred.

In other desirable forms of this invention, the composition may be substantially solid or pasty in character, such as toothpowder, a dental tablet or a toothpaste (dental cream) or gel dentifrice. The vehicle of such solid or pasty oral preparations generally contains dentally acceptable polishing material. Examples of polishing materials are water-insoluble sodium metaphosphate, potassium metaphosphate, tricalcium phosphate, dihydrated calcium phosphate, anhydrous dicalcium phosphate, calcium pyrophosphate, magnesium orthophosphate, trimagnesium phosphate, calcium carbonate, hydrated alumina, calcined alumina, aluminium silicate, zirconium silicate, silica, bentonite, and mixtures thereof. Other suitable polishing material include the particulate thermosetting resins such as melamine-, phenolic, and urea-formaldehydes, and cross-linked polyepoxides and polyesters. Preferred polishing materials include crystalline silica having particle sizes of up to about 5 microns, a mean particle size of up to about 1.1 microns, and a surface area of up to about 50,000 cm²/g, silica gel or colloidal silica, and complex amorphous alkali metal aluminosilicate.

When visually clear gels are employed, a polishing agent of colloidal silica, such as those sold under the trademark SYLOID as Syloid 72 and Syloid 74 or under the trademark SANTOCEL as Santocel 100, alkali metal aluminosilicate complexes are particularly useful since they have refractive indices close to the refractive indices of gelling agent-liquid (including water and/or humectant) systems commonly used in dentifrices.

Many of the so-called "water insoluble" polishing materials are anionic in character and also include small amounts of soluble material. Thus, insoluble sodium metaphosphate may be formed in any suitable manner, for example as illustrated by Thorpe's Dictionary of Applied Chemistry, Volume 9, 4th Edition, pp. 510-511. The forms of insoluble sodium metaphosphate known as Madrell's salt and Kurrol's salt are further examples of suitable materials. These metaphosphate salts exhibit only a minute solubility in water, and therefore are commonly referred to as insoluble metaphosphates (IMP). There is present therein a minor amount of soluble phosphate material as impurities, usually a few percent such as up to 4% by weight. The amount of soluble phosphate material, which is believed to include a soluble sodium trimetaphosphate in the case of insoluble metaphosphate, may be reduced or eliminated by washing with water if desired. The insoluble alkali metal metaphosphate is typically employed in powder form of a particle size such that no more than 1% of the material is larger than 37 microns.

The polishing material is generally present in the solid or pasty compositions in weight concentrations of about 10% to about 99%. Preferably, it is present in amounts from about 10% to about 75% in toothpaste, and from about 70% to about 99% in toothpowder. In toothpastes, when the polishing material is silicious in nature, it is generally present in an amount of about 10-30% by weight. Other polishing materials are typically present in amount of about 30-75% by weight.

In a toothpaste, the liquid vehicle may comprise water and humectant typically in an amount ranging from about 10% to about 80% by weight of the preparation. Glycerine, propylene glycol, sorbitol and polypropylene glycol exemplify suitable humectants/carriers. Also advantageous are liquid mixtures of water, glycerine and sorbitol. In clear gels where the refractive index is an important consideration, about 2.5-30% w/w of water, 0 to about 70% w/w of glycerine and about 20-80% w/w of sorbitol are preferably employed.

Toothpaste, creams and gels typically contain a natural or synthetic thickener or gelling agent in proportions of about 0.1 to about 10, preferably about 0.5 to about 5% w/w. A suitable thickener is synthetic hectorite, a synthetic colloidal magnesium alkali metal silicate complex clay available for example as Laponite (e.g. CP, SP 2002, D) marketed by Laporte Industries Limited. Laponite D is, approximately by weight 58.00% $SiO_2$, 25.40% MgO, 3.05% $Na_2O$, 0.98% $Li_2O$, and some water and trace metals. Its true specific gravity is 2.53 and it has an apparent bulk density of 1.0 g/ml at 8% moisture.

Other suitable thickeners include Irish moss, iota carrageenan, gum tragacanth, starch, polyvinylpyrrolidone, hydroxyethylpropylcellulose, hydroxybutyl methyl cellulose, hydroxypropyl methyl cellulose, hydroxyethyl cellulose (e.g. available as Natrosol), sodium carboxymethyl cellulose, and colloidal silica such as finely ground Syloid (e.g. 244). Solubilizing agents may also be included such as humectant polyols such propylene glycol, dipropylene glycol and hexylene glycol, cellosolves such as methyl cellosolve and ethyl cellosolve, vegetable oils and waxes containing at least about 12 carbons in a straight chain such as olive oil, castor oil and petrolatum and esters such as amyl acetate, ethyl acetate and benzyl benzoate.

It will be understood that, as is conventional, the oral preparations will usually be sold or otherwise distributed in suitable labelled packages. Thus, a jar of mouth rinse will have a label describing it, in substance, as a mouth rinse or mouthwash and having directions for its use; and a toothpaste, cream or gel will usually be in a collapsible tube, typically aluminium, lined lead or plastic, or other squeeze, pump or pressurized dispenser for metering out the contents, having a label describing it, in substance, as a toothpaste, gel or dental cream.

Organic surface-active agents may be used in the compositions of the present invention to achieve increased prophylactic action, assist in achieving thorough and complete dispersion of the active agent throughout the oral cavity, and render the instant compositions more cosmetically acceptable. The organic surface-active material is preferably anionic, non-ionic or ampholytic in nature and preferably does not interact with the active agent. It is preferred to employ as the surface-active agent a detersive material which imparts to the composition detersive and foaming properties. Suitable examples of anionic surfactants are water-soluble salts of higher fatty acid monoglyceride monosulfates, such as the sodium salt of the monosulfated monoglyceride of hydrogenated coconut oil fatty acids, higher alkyl sulfates such as sodium lauryl sulfate, alkyl aryl sulfonates such as sodium dodecyl benzene sulfonate, higher alkylsulfo-acetates, higher fatty acid esters of 1,2-dihydroxy propane sulfonate, and the substantially saturated higher aliphatic acyl amides of lower aliphatic amino carboxylic acid compounds, such as those having 12 to 16 carbons in the fatty acid, alkyl or acyl radicals, and the like. Examples of the last mentioned amides are N-lauroyl sarcosine, and the sodium, potassium, and ethanolamine salts of N-lauroyl, N-myristoyl, or N-palmitoyl sarcosine which should be substantially free from soap or similar higher fatty acid material. The use of these sarconite compounds in the oral compositions of the present invention is particularly advantageous since these materials exhibit a prolonged marked effect in the inhibition of acid formation in the oral cavity due to carbohydrates breakdown in addition to exerting some reduction in the solubility of tooth enamel in acid solutions. Examples of water-soluble non-ionic surfactants suitable for use are condensation products of ethylene oxide with various reactive hydrogen-containing compounds reactive therewith having long hydrophobic chains (e.g. aliphatic chains of about 12 to 20 carbon atoms), which condensation products ("ethoxamers") contain hydrophilic polyoxyethylene moieties, such as condensation products of poly (ethylene oxide) with fatty acids, fatty alcohols, fatty amides, polyhydric alcohols (e.g. sorbitan monostearate) and polypropyleneoxide (e.g. Pluronic materials).

The surface active agent is typically present in amount of about 0.1-5% by weight. It is noteworthy, that the surface active agent may assist in the dissolving of the active agent of the invention and thereby diminish the amount of solubilizing humectant needed.

Various other materials may be incorporated in the oral preparations of this invention such as whitening agents, preservatives, silicones, chlorophyll compounds and/or ammoniated material such as urea, diammonium phosphate, and mixtures thereof.

These adjuvants, where present, are incorporated in the preparations in amounts which do not substantially adversely affect the properties and characteristics desired.

Any suitable flavouring or sweetening material may also be employed. Examples of suitable flavouring constituents are flavouring oils, e.g. oil of spearmint, peppermint, wintergreen, sassafras, clove, sage, eucalyptus, marjoram, cinnamon, lemon, and orange, and methyl salicylate. Suitable sweetening agents include sucrose, lactose, maltose, sorbitol, xylitol, sodium cyclamate, perillartine, AMP (aspartyl phenyl alanine, methyl ester), saccharine, and the like. Suitably, flavour and sweetening agents may each or together comprise from about 0.1% to 5% more of the preparation.

The compositions of this invention can also be incorporated in lozenges, or in chewing gum or other products, e.g. by stirring into a warm gum base or coating the outer surface of a gum base, illustrative of which are jelutong, rubber latex, vinylite resins, etc., desirably with conventional plasticizers or softeners, sugar or other sweeteners or such as glucose, sorbitol and the like. The composition of the invention may be a dual phase composition wherein each phase permits release of components over different time periods. For example, in use a dual phase composition may release stannous-associated stabilized ACP and/or stannous-associated stabilized ACFP, preferably CPP-ACP/$SnF_2$ and/or CPP-ACFP/$SnF_2$, from a first phase at a faster rate than a compound that is capable of increasing or maintaining the pH of a solution from a second phase. Preferably, the dual phase composition is a dual phase chewing gum.

An alternative composition may be one that provides stabilized ACP or ACFP and a stannous compound that then in situ, such as the oral cavity, forms stannous-associated stabilized ACP or ACFP. An exemplary composition may be a chewing gum that contains stabilized ACP or ACFP in the pellet and a stannous compound in the centre chew.

In a further aspect, the invention provides compositions including pharmaceutical compositions comprising any of the (a) compositions including a stannous compound and stabilized ACP or ACFP, or (b) a stannous-associated stabilized ACP or ACFP complexes as described above together with a compound capable of increasing or maintaining the pH of a solution and a pharmaceutically-acceptable carrier. Such compositions may be selected from the group consisting of dental, anticariogenic compositions and therapeutic compositions. Dental compositions or therapeutic compositions may be in the form of a gel, liquid, solid, powder, cream or lozenge. Therapeutic compositions may also be in the form of tablets or capsules. In one embodiment, the stannous-associated stabilized ACP or ACFP complexes are substantially the only remineralizing active components of such a composition. For example, a crème formulation may be employed containing: water; glycerol; CPP-ACP/$SnF_2$; D-sorbitol; silicon dioxide; sodium carboxymethylcellulose (CMC—Na); propylene glycol; titanium dioxide; xylitol; phosphoric acid; guar gum; zinc oxide; sodium saccharin; ethyl p-hydroxybenzoate; magnesium oxide; butyl p-hydroxybenzoate and propyl p-hydroxybenzoate.

The invention further includes a formulation described above provided together with instructions for its use to treat or prevent any one or more of dental caries or tooth decay, dental erosion and fluorosis, dentinal hypersensitivity, dental plaque, gingivitis or periodontitis.

In another embodiment, the compositions of the invention as described herein do not include a phosphate buffer and/or a calcium chelator. For example, any dentifrice described herein may not include a phosphate buffer and/or a calcium chelator.

In an embodiment of the present invention there is provided a composition for dental mineralization including stannous-associated stabilized ACP or ACFP complexes, wherein the composition does not include a phosphate buffer and/or calcium chelator.

In another embodiment, the compositions of the invention as described herein do not include a viscosity regulator, or a viscosity regulator at 0.5 to 50%.

In another embodiment, the compositions of the invention as described herein do not include sodium carboxymethylcellulose, or 0.01 to 10% sodium carboxymethylcellulose having the esterification degree of 0.7 to 1.0.

In one embodiment, the active components of the composition consist essentially of the stannous-associated stabilized ACP or ACFP complexes.

In a further aspect, there is provided a method of treating or preventing one or more of each of dental caries, tooth decay, dental erosion and fluorosis, dentinal hypersensitivity, dental plaque, gingivitis and periodontitis comprising the steps of administering (a) a composition including a stannous compound and stabilized ACP or ACFP, or (b) a stannous-associated stabilized ACP or ACFP complexes, to the teeth of a subject. Topical administration of the complex is preferred. The method preferably includes the administration of the complex in a formulation as described above.

In a further aspect there is provided the use of (a) compositions including a stannous compound and stabilized ACP or ACFP, or (b) a stannous-associated stabilized ACP or ACFP complexes in a manufacture of a composition for the treatment and/or prevention of one or more of dental caries, tooth decay, dental erosion and fluorosis, dental hypersensitivity, dental plaque, gingivitis and periodontitis.

According to a further aspect of the invention there is provided a composition for dental restoration, including a dental restorative material to which has been added (a) a composition including a stannous compound and stabilized ACP or ACFP, or (b) a stannous-associated stabilized ACP or ACFP complexes. The base of the dental restorative material can be a glass ionomer cement, a composite material or any other restorative material which is compatible. A glass ionomer cement is preferred. It is preferred that the amount of stabilised stannous-associated stabilized ACP or ACFP complexes, preferably CPP-ACP/$SnF_2$ complex or CPP-ACFP/$SnF_2$ complex, included in the dental restorative material is 0.01-80% by weight, preferably 0.5-10% and more preferably 1-5% by weight. The dental restorative material of this invention which contains the above mentioned agents may be prepared and used in various forms applicable to dental practice. The dental restorative material according to this embodiment may further include other ions, eg. antibacterial ions $Zn^{2+}$, $Ag^+$, etc or other additional ingredients depending on the type and form of a particular dental restorative material. It is preferable that the pH of dental restorative material according to this embodiment be between 2-10, more preferably 5-9 and even more preferably 5-7. It is preferable that the pH of the dental restorative material containing a stannous-associated stabilized ACP or ACFP complex be in the range of about 2 to 10, more preferably in the range of about 5 to 9 and even more preferably in the range of about 5 to 7.

It will be clearly understood that, although this specification refers specifically to applications in humans, the invention is also useful for veterinary purposes. Thus in all aspects the invention is useful for domestic animals such as cattle, sheep, horses and poultry; for companion animals such as cats and dogs; and for zoo animals.

One example of a mineralizing composition comprises the following (in decreasing order of proportion):

water
glycerol
CPP-ACP/$SnF_2$
D-sorbitol
silicon dioxide
sodium carboxymethylcellulose (CMC—Na)
propylene glycol
titanium dioxide
xylitol
phosphoric acid
guar gum
zinc oxide
sodium saccharin
ethyl p-hydroxybenzoate
magnesium oxide
butyl p-hydroxybenzoate
propyl p-hydroxybenzoate The invention will now be further described with reference to the following non-limiting examples.

Example 1

Casein phosphopeptide-amorphous calcium phosphate (CPP-ACP) was acquired from Cadbury Enterprises Pte Ltd under the trademark name Recaldent™. A solution was prepared using CPP-ACP, $SnF_2$ and NaF to produce at 0.4% w/v CPP-ACP, 220 ppm F as $SnF_2$ and 70 ppm F as NaF, pH 5.6. Specifically, the CPP-ACP/$SnF_2$ complexes were prepared by adding CPP-ACP to distilled/deionised water and then $SnF_2$ (solid) and NaF added with addition of 1 M HCl to maintain the pH between 4.0-6.5. The pH was not allowed to go above 6.5. The total volume of acid added was less than 1% of the CPP-ACP/$SnF_2$ solution volume. This solution was designated stabilized $SnF_2$/ACP. While NaF was added in this method it is a minor component and the majority of the fluoride derives from the $SnF_2$. The method could be performed using $SnF_2$ only (without NaF). Another solution was prepared using CPP-ACP and NaF to produce 0.4% w/v CPP-ACP, and 290 ppm F as NaF, pH 5.6. This solution was designated stabilized NaF/ACP.

Both solutions were stable at room temperature (20° C.) for many months with no precipitate. Both solutions were tested for their ability to remineralize enamel subsurface lesions. Human tooth enamel demineralized subsurface lesions were prepared in third molar enamel blocks using the method of Reynolds, (1997). J Dent Res 76:1587-1595. Half the blocks were remineralized by suspending them individually in the stabilized $SnF_2$/ACP solution and the other half in the stabilized NaF/ACP solution for 7 days at 37° C. After remineralization the enamel blocks were embedded, sectioned and subjected to transverse microradiography and densitometric image analysis as previously described by Reynolds (1997) to determine percent mineral content gain (% Remineralization) shown in Table 2. A one way analysis of variance with differences in means determined using a Tukey HSD post hoc comparison showed that the treatment with stabilized $SnF_2$/ACP solution significantly increased the level of remineralization by 32%.

TABLE 2

Remineralization of enamel subsurface lesions by stabilized $SnF_2$/ACP versus stabilized NaF/ACP.

| Solution | % Remineralization |
|---|---|
| Stabilized $SnF_2$/ACP<br>[0.4% w/v CPP-ACP<br>220 ppm F as $SnF_2$<br>70 ppm F as NaF] | 46.1 ± 5.7* |
| Stabilized NaF/ACP<br>[0.4% w/v CPP-ACP<br>290 ppm F as NaF] | 35.0 ± 5.4 |

*significantly different $p < 0.01$

Figure 3:
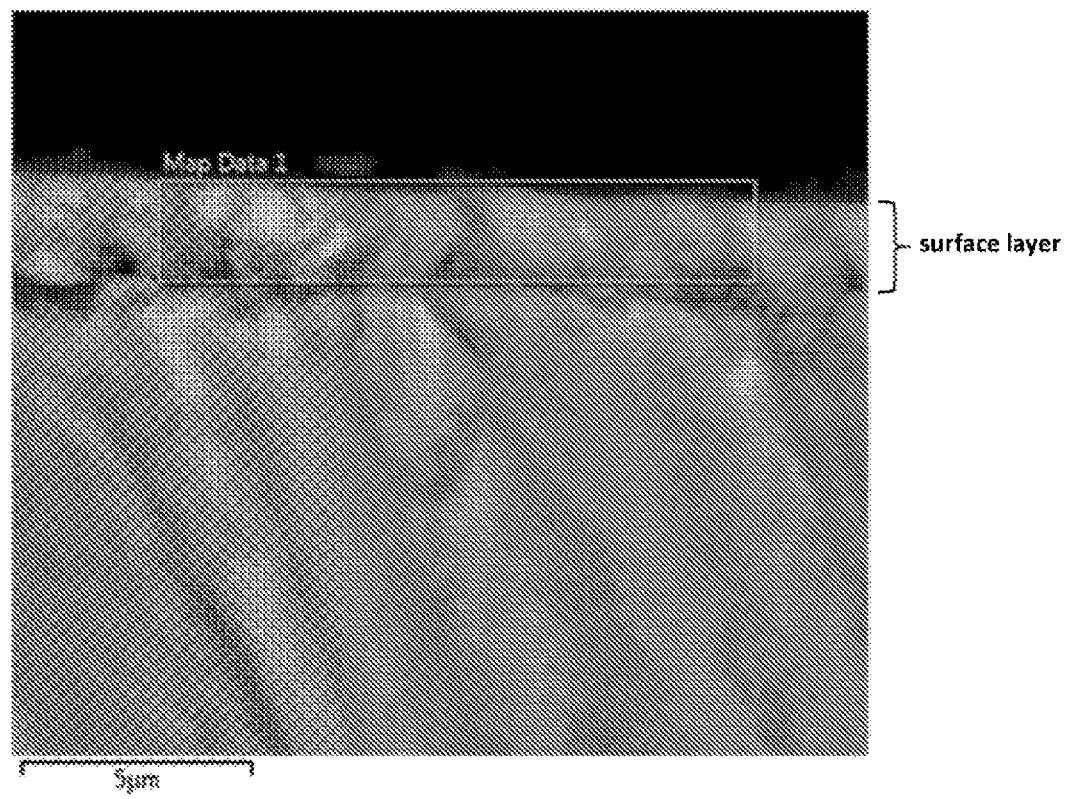
FIG. 3: Scanning Electron Microscopy-Energy Dispersive Spectroscopy (SEM-EDS) of the mineralised surface layer resulting from treatment with stabilized $SnF_2$/ACP.
Figure 4:
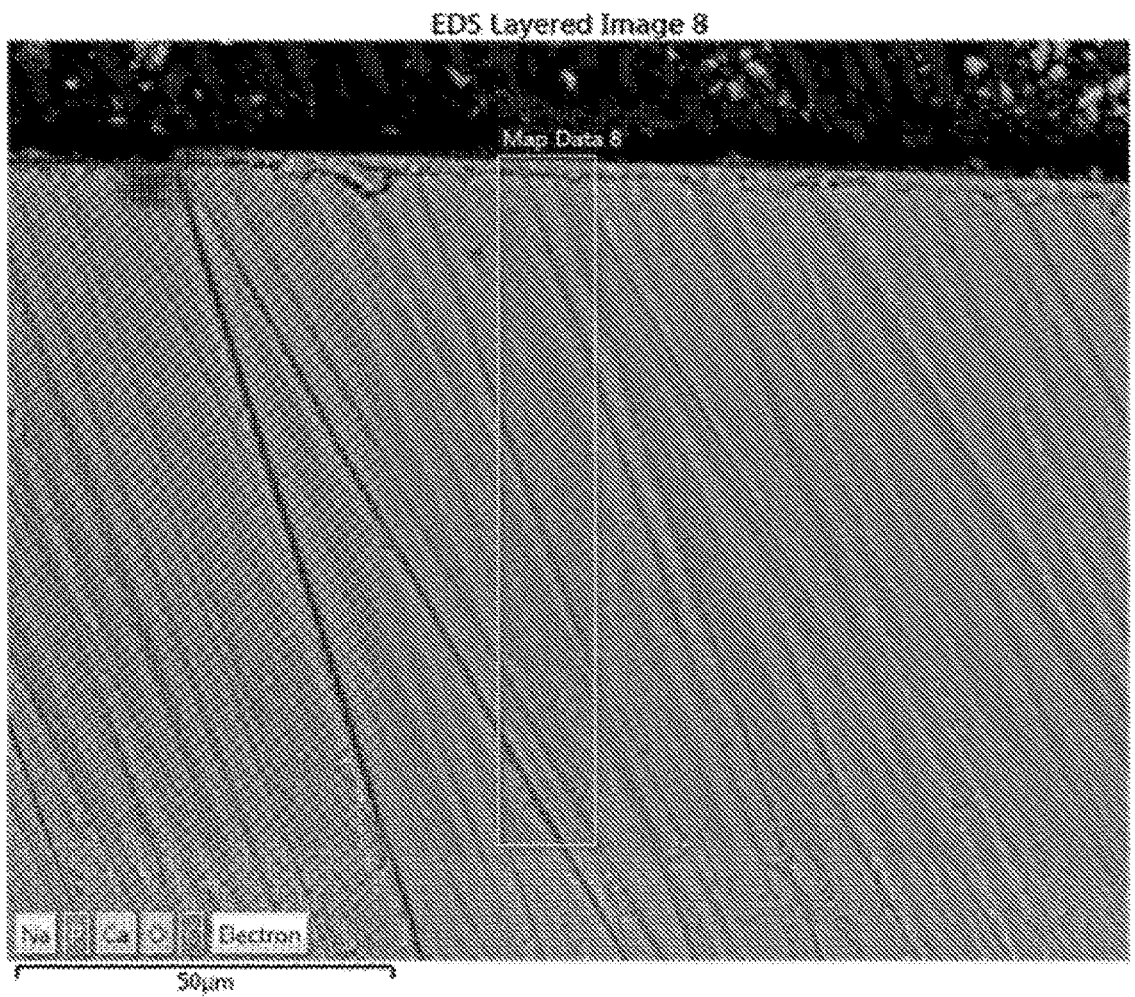
FIG. 4: Representative SEM image of elemental analysis by SEM-EDS of the mineralised surface layer resulting from treatment with stabilized $SnF_2$/ACP.
Figure 5:
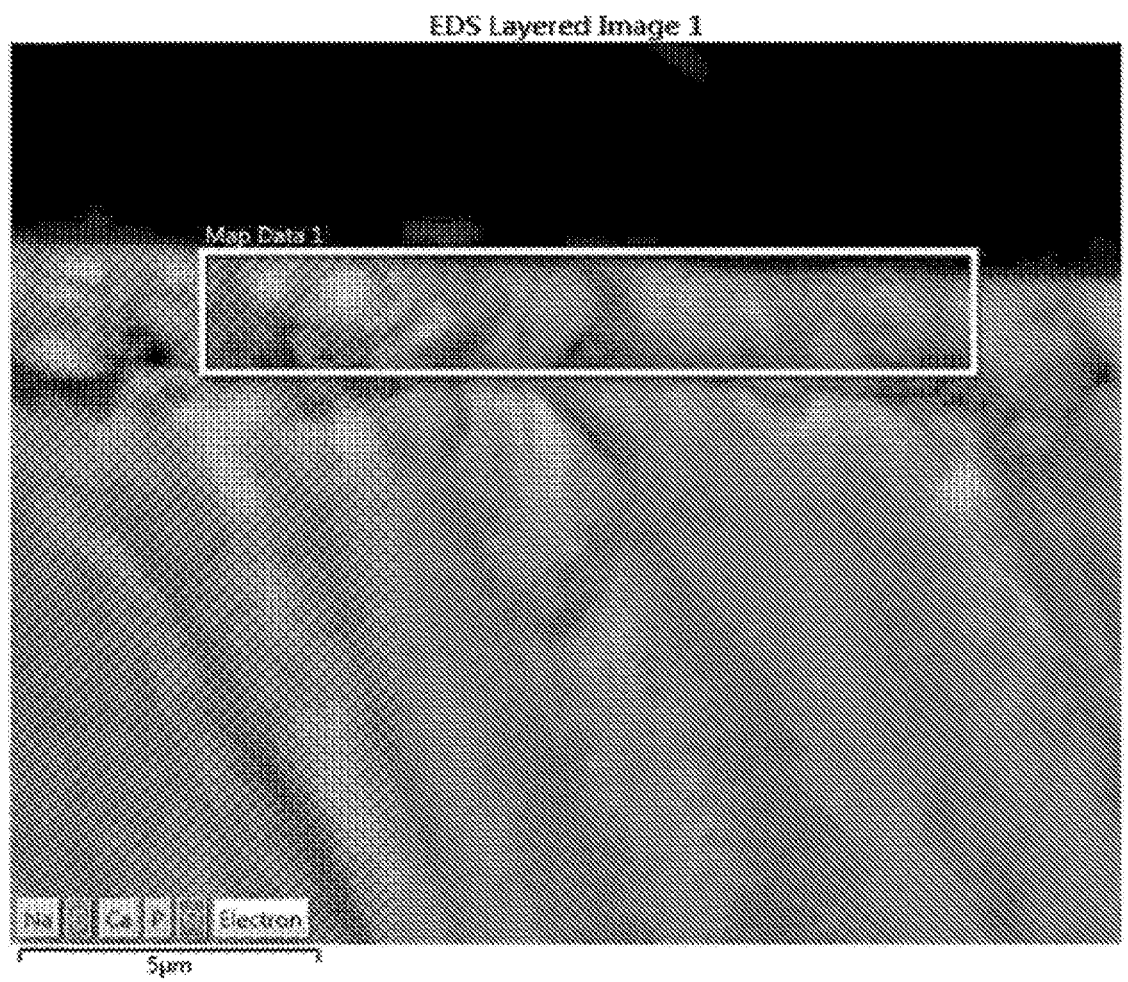
FIG. 5: Representative SEM image of elemental analysis by SEM-EDS of the mineralised surface layer resulting from treatment with stabilized $SnF_2$/ACP.
Figure 6:
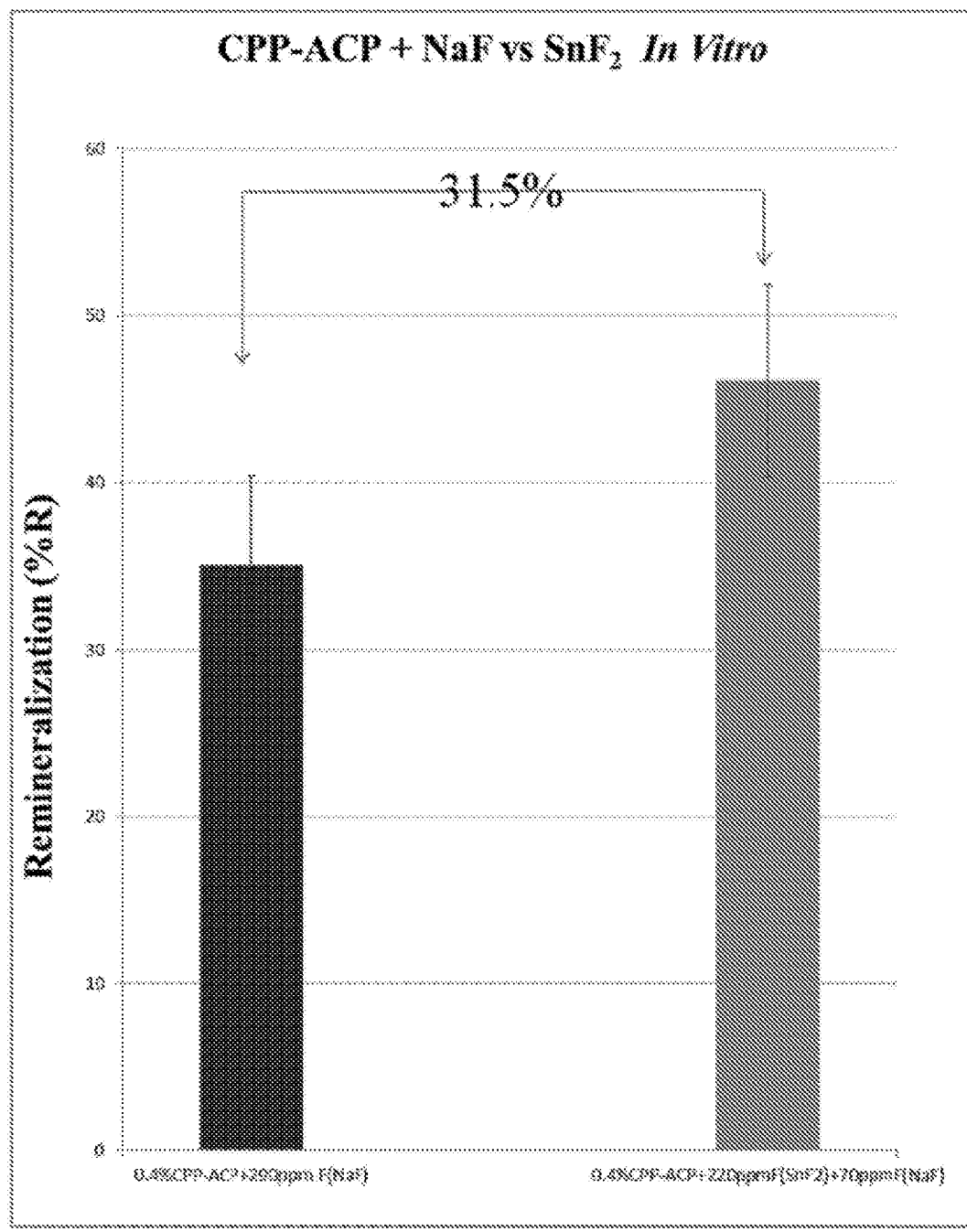
FIG. 6: Remineralization of enamel subsurface lesions by stabilized $SnF_2$/ACP versus stabilized NaF/ACP. The numerical values of this Figure are shown in Table 2.

Analysis of the enamel lesions using scanning electron microscopy (FIGS. 1 and 2) revealed that the lesions treated with the stabilized $SnF_2$/ACP further had a surface layer. Surprisingly the stabilized $SnF_2$/ACP formulation produced significantly greater enamel subsurface lesion remineralization (Table 2) and appeared also to form a protective surface layer demonstrating the unexpected superiority of the stabilized $SnF_2$/ACP formulation. An experiment using scanning electron microscopy-energy dispersive spectroscopy (SEM-EDS) of the surface layer (FIG. 3 and Table 3) confirmed that it was apatite. The surface layer EDS analysis showed it contained 10.33 wt % P and 21.18 wt % Ca giving a typical apatite Ca:P wt % ratio of 2.05. The sound enamel contained 15.26 wt % P and 30.99 wt % Ca giving the same typical apatite Ca:P wt % ratio of 2.03.

These data show that the surface layer is composed of apatite, however the surface layer had higher Sn (1.23 wt % versus 0 wt % for sound enamel) and fluoride (0.54 wt % versus 0.11% for sound enamel). This of course is consistent with the CPP-stabilised $SnF_2$/ACP solution containing Sn and F. CPP was also involved in the formation of the surface layer as the C was 26.53 wt % in the surface layer but only around 10 wt % in the sound enamel (Table 4). This supports the mechanism whereby the stannous ions can cross-link the phosphopeptide stabilized ACP or stabilized ACFP at the tooth surface to form a layer that can protect the tooth surface from demineralization.

These results indicate that the CPP-stabilised $SnF_2$/ACP treatment has not only produced substantially better subsurface remineralization but it has also produced a uniform, protective surface layer.

The retention of stannous-associated stabilized ACP or ACFP in a cross-linked surface layer would (i) protect from tooth sensitivity as it would seal dentinal tubules, (ii) protect from plaque formation as it contains the antibacterial ion Sn and (iii) protect from dental erosion and dental caries. It would also promote subsurface remineralization. Without being bound by any theory or mechanism of action it appears that stannous ions help to promote the surface layer by cross-linking the CPP-ACP or CPP-ACFP at the surface of the enamel.

TABLE 3

Elemental analysis by SEM-EDS of the mineralised surface layer resulting from treatment with stabilized $SnF_2$/ACP.

| Element | $SnF_2$/ACP Surface Layer (wt %) | Normal Sound Enamel (wt %) |
|---|---|---|
| C | 26.53 | 12.28 |
| O | 39.59 | 40.59 |
| F | 0.54 | 0.11 |
| Na | 0.31 | 0.47 |
| P | 10.33 | 15.26 |
| Cl | 0.29 | 0.30 |
| Ca | 21.18 | 30.99 |
| Sn | 1.23 | 0 |
| TOTAL | 100 | 100 |

A more detailed scanning electron microscopy-energy dispersive spectroscopy (SEM-EDS) analysis of the various layers wherein the embedding resin is excluded is shown in Table 4. This shows that the high carbon content in the sound enamel in Table 3 is including the resin. When the resin was excluded, the carbon content of sound enamel was in the range of 6 to 10 wt %. The carbon content of the surface layer produced by the CPP-stabilised $SnF_2$/ACP treatment was almost 3-fold greater than sound enamel indicating that the phosphopeptides are present in the layer. The protective surface layer formed by the stannous-associated stabilized ACP complexes provides a source of fluoride as the level of fluoride in the mineralised surface layer is 5 fold greater than the level of fluoride in sound enamel. Further, the level of fluoride present is greater than that present in the remineralized lesion. The level of stannous present in the surface layer was significantly higher, 12 fold, than the remineralized lesion.

The level of fluoride in the lesion remineralized with the stannous associated ACP is greater than CPP-ACP and sodium fluoride. Further, there was an increase in calcium present in the lesion remineralized by the stannous-associated stabilized ACP compared to the CPP-ACP and sodium fluoride. This level of calcium is approaching the level of calcium present in sound enamel.

TABLE 4

Detailed elemental analysis by SEM-EDS of the mineralised surface layer resulting from treatment with CPP stabilized SnF2/ACP.

| Element wt % | Sound Enamel | Demineralised Lesion | CPP-ACP/NaF Remineralised Lesion | CPP-ACP/$SnF_2$ Remineralised Lesion | CPP-ACP/$SnF_2$ Mineralised Surface Layer |
|---|---|---|---|---|---|
| C | 6-10[a] | ND[b] | ND | 17.49 ± 0.59 | 26.53 ± 0.44 |
| O | 40.59 ± 0.63 | 38.14 ± 0.32 | 37.94 ± 10.44 | 37.93 ± 0.49 | 39.59 ± 0.38 |

TABLE 4-continued

Detailed elemental analysis by SEM-EDS of the mineralised surface layer resulting from treatment with CPP stabilized SnF2/ACP.

| Element wt % | Sound Enamel | Demineralised Lesion | CPP-ACP/NaF Remineralised Lesion | CPP-ACP/SnF$_2$ Remineralised Lesion | CPP-ACP/SnF$_2$ Mineralised Surface Layer |
|---|---|---|---|---|---|
| F | 0.11 ± 0.31 | 0.12 ± 0.12 | 0.21 ± 0.16 | 0.34 ± 0.23 (3.1 fold increase) | 0.54 ± 0.19 (5 fold increase) |
| P | 15.26 ± 0.26 | 13.64 ± 0.13 | 14.05 ± 0.18 | 14.02 ± 0.19 | 10.33 ± 0.13 |
| Ca | 30.99 ± 0.44 | 27.97 ± 0.21 | 28.49 ± 0.29 | 29.25 ± 0.33 | 21.18 ± 0.21 |
| Sn | <0.1 | 0.13 ± 0.13 | 0.11 ± 0.17 | 0.24 ± 0.2 (2.4 fold increase) | 1.23 ± 0.16 (12.3 fold increase) |
| Ca:P | 2.031[c] | 2.051 | 2.028 | 2.086 | 2.050 |

[a]Sabel et al. Scientific World Journal (2012)
[b]ND = not yet determined
[c]Ca:P wt % ratio for HA = 2.157 and for ACP = 1.941

Example 2

This example describes the experimental protocol for the measurement of CPP-bound (tightly bound), loosely bound and free ions in solution A sample of each solution prepared in Example 1 was taken and less than 10% collected as a filtrate using a 3000 molecular weight cut-off Centriprep 3 ultrafiltration membrane. The Centripreps containing the samples were centrifuged at 1,000 g for 15 min in a Beckman J2-21 centrifuge using a JA 10.5 rotor. The original sample before Centriprep centrifugation and a sample of the filtrate after Centriprep centrifugation were taken for analysis of calcium, phosphate fluoride and stannous concentrations. The analysis of the original sample gave total calcium, phosphate, fluoride and stannous ion concentrations and the analysis of the filtrate gave free (unbound) calcium, phosphate and fluoride concentrations. The difference between the total and unbound concentrations is the bound concentration of Ca, Pi, F and Sn by the CPP.

Example 3

A topical crème may be produced in accordance with the present invention having the following ingredients:
Water
glycerol
Stabilised SnF$_2$/ACP and/or SnF$_2$/ACFP
D-sorbitol
sodium carboxymethylcellulose (CMC—Na)
propylene glycol
silicon dioxide
titanium dioxide
xylitol
phosphoric acid
sodium fluoride
flavouring
sodium saccharin
ethyl p-hydroxybenzoate
propyl p-hydroxybezoate
butyl p-hydroxybenzoate Example 4

A mouthrinse formulation may be produced in accordance with the present invention having the following composition:
Water
Alcohol
Poloxamer 407
Sodium Lauryl Sulphate
Stabilised SnF$_2$/ACP and/or SnF$_2$/ACFP
Sodium Fluoride
Flavours
Sodium Saccharin
Ethyl p-hydroxybenzoate
Propyl p-hydroxybenzoate
Butyl p-hydroxybenzoate Example 5

A sugar-free chewing gum formulation may be produced in accordance with the present invention having the following composition:
Crystalline sorbitol/mannitol/xylitol
Gum base
Calcium carbonate
Glycerine
Stabilised SnF$_2$/ACP and/or SnF$_2$/ACFP
Sodium Fluoride
Flavour oil
Water Example 6

The following is a protocol for CPP stabilized ACP/SnF$_2$ solution ion analysis. Total (tightly & loosely-bound) and loosely-bound samples were prepared as follows:

Total (tightly and loosely-bound): One ml of 0.4% CPP-ACP/220 ppm F (as SnF$_2$)/70 ppm F (as NaF) solution was taken and placed into 19 ml of 1 M HNO3 and incubated at room temperature with constant slow end over end mixing for 24 hrs (20 rpm). The mixture was centrifuged at 1000 g for 15 minutes at room temperature. The supernatant was analyzed for calcium, stannous, phosphate and fluoride.

Loosely-bound: A sample of the 0.4% CPP-ACP/220 ppm F (as SnF$_2$)/70 ppm F (as NaF) solution was taken and placed in a centricon with a 1000 MWCO filter and centrifuged at 3000 g for 1 hour at room temperature to produce enough filtrate (<10% of total sample to not affect equilibrium) for analysis by atomic absorption spectrophotometry (AAS) and ion chromatography (IC). The filtrates were then measured to give loosely-bound ions.

The total and loosely bound calcium, stannous, phosphate and fluoride in the solution were determined by ion chromatography (for fluoride and phosphate) and Atomic Absorption Spectrometry (for calcium and stannous).

CPP tightly-bound (colloidal retentate) ions were calculated from the difference between Total and loosely-bound (as explained above). Based on this example, the stannous-associated ACP complex had a stannous ion content of about 6 to 8 mole per mole of phosphopeptide.

TABLE 5

Ion analysis of 0.4% CPP-ACP/220 ppm F as $SnF_2$/70 ppm F as NaF solution at pH 5.5 and pH 4.0 by Atomic Absorption Spectrometry (for stannous and calcium) and Ion Chromatography (for fluoride and phosphate).

|  | pH | Ca μM | Pi μM | Sn μM | F ppm |
|---|---|---|---|---|---|
| Total | 5.5 | 16160.0 ± 83.1 | 8380.0 ± 385.5) | 5582.2 ± 140.3 | 292.5 ± 1.7 |
|  | 4.0 | 17045.3 ± 92.4 | 8670.0 ± 157.4 | 5672.1 ± 118.3 | 289.5 ± 12.0 |
| Tightly-bound | 5.5 | 15389 (95.2%) | 7688 (91.7%) | 5545 (99.3%) | 120.2 (41.1%) |
|  | 4.0 | 13788 (80.9%) | 5499 (63.4%) | 5150 (90.8%) | 164.2 (56.7%) |
| Loosely-bound | 5.5 | 770.7 ± 6.5 (4.8%) | 692.0 ± 193.5 (8.3%) | 37.1 ± 3.4 (0.7%) | 172.3 ± 2.7 (58 9%) |
|  | 4.0 | 3257.1 ± 16.4 (19.1%) | 3170.7 ± 55.1 (36.6%) | 522.3 ± 13.4 (9.2%) | 125.3 ± 1.1 (43.3%) |

Example 7

This in situ study was designed to compare remineralization using an established intra-oral remineralization model promoted by five solutions:
1) 0.4% (w/v) calcium phosphopeptide stabilised-amorphous calcium phosphate (CPP-ACP), 220 ppm stannous fluoride ($SnF_2$) and 70 ppm sodium fluoride (NaF) (shown in FIG. 7 as 2% CPP-ACP+$SnF_2$);
2) 0.4% (w/v) CPP-ACP and 290 ppm NaF;
3) 0.4% (w/v) CPP-ACP;
4) 220 ppm $SnF_2$ and 70 ppm NaF without CPP-ACP (shown in FIG. 7 as $SnF_2$); and
5) 290 ppm NaF.

In this model subjects wear a palatal appliance and rinse 4 times a day with 5 mL of solution for five 14 consecutive-day treatment periods (including weekends) and rinsing with a different solution during each treatment period.

This randomised controlled study used a double-blind, five-way crossover design to assess the effects of five solutions to enhance enamel remineralization using an intra-oral remineralization model. Each solution contained the same amount of 290 ppm F (equivalent to 1450 ppm F in a toothpaste diluted 1 in 5) [see above]. Subjects were randomly allocated to one of the five solutions for the first treatment period and, after a one-week washout rest period, crossed over to another solution for the second treatment period. This was repeated for the five treatments. Each subject wore a custom made palatal appliance containing four pre-sterilised enamel slabs containing artificially-created subsurface lesions and four times a day for 14 consecutive days including weekends (treatment period) rinsed for one minute with 5 mL of their allocated solution then expectorated all the solution and accumulated saliva and continued to wear their appliance. The four rinses per day were performed (i) after breakfast, (ii) after lunch, (iii) after dinner and (iv) before retiring at night. After the first rinse per day of each treatment period subjects on three different days expectorated the solution and accumulated saliva into a clean tube for ion analysis. Subjects kept a diary of times and duration they rinsed with their solutions. Subjects were instructed to maintain their normal diet and oral hygiene procedures for the duration of the treatment periods. Appliances were removed during subjects normal oral hygiene procedures during the study period. After removing the appliances for oral hygiene procedures, subjects cleaned their appliances as instructed with a toothbrush and fluoride-free denture paste (both supplied) avoiding the trough areas and gently rinsed their appliances with DDW before replacing the appliances. When out of the mouth the appliances were stored in sealed humid containers. AU subjects brushed their teeth with standard fluoride toothpaste provided by the sponsor for the duration of the study. The subjects returned to the clinical site with their appliances and diary at the conclusion of each 14-day treatment period.

Figure 7:
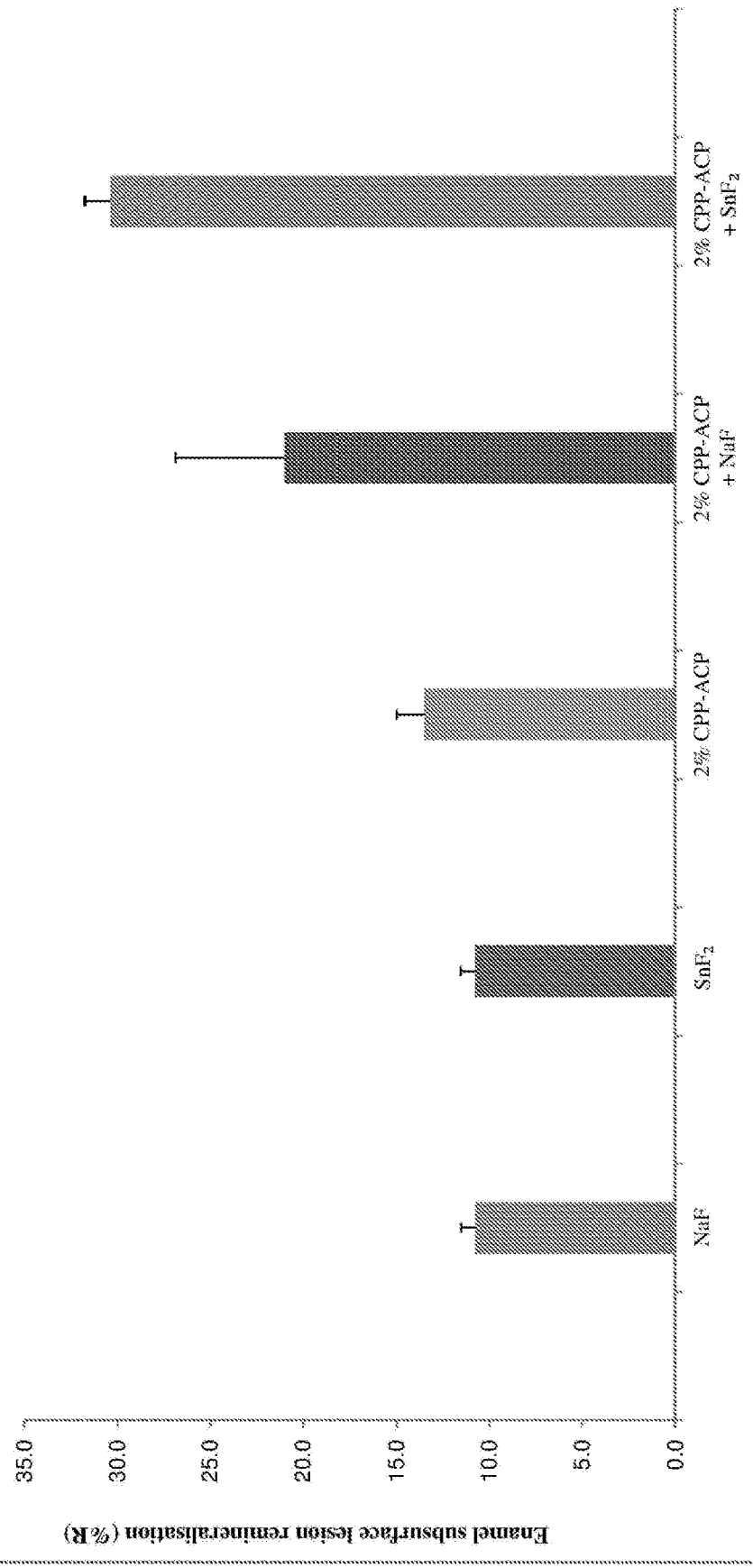
FIG. 7: In situ remineralization of enamel subsurface lesions by CPP-ACP $SnF_2$/NaF compared with CPP-ACP, $SnF_2$ and NaF, NaF with or without CPP-ACP.

The researchers did not know which treatment had been administered nor the subject. Neither the researchers, nor the recorder had access to the treatment code. Personnel dispensing the test solutions or supervising their use did not participate in the examination of the enamel half-slabs in order to minimize potential bias. Following the baseline examination, subjects were assigned a subject number. Subject numbers were recorded on their case report forms. Subjects were randomly assigned to use one of the solutions during the first treatment period then crossed over to another solution for the second to fifth treatment period. Randomisation was effected using a standard randomisation table for the number of treatments in the crossover study. Results of the in situ study are shown in FIG. 7. These results show that in an in situ model a solution including stannous-associated stabilized complexes (as 2% CPP-ACP, with stannous fluoride and sodium fluoride, far right column, also referred to herein as stabilized $SnF_2$/ACP) provide a significantly greater level of enamel subsurface remineralization compared to sodium fluoride alone, stannous fluoride & sodium fluoride, CPP-ACP alone or CPP-ACP with sodium fluoride. The two far right columns labelled 2% CPP-ACP+NaF and 2% CPP-ACP+$SnF_2$ were significantly different (p<0.01). This clearly demonstrates that in vivo in the oral cavity the stannous-associated stabilized complexes of the invention have a superior capacity to remineralize lesions.

A palatal appliance for each subject was prepared by taking alginate impressions of upper and lower dental arches from which study models were produced and articulated. Removable palatal acrylic appliances covering the first premolars to the last tooth in the arch were fabricated for each subject. The appliance consisted of a palatal plate that was retained in the mouth by four stainless steel clasps. Troughs on each side of the appliance adjacent to the palatal surface of maxillary premolar/molar teeth accommodated two enamel half-slabs containing demineralised subsurface lesions. Therefore, each appliance contained four enamel half-slabs. The appliances was designed to ensure its surfaces were smooth and comfortable for the subjects.

Extracted third molars were obtained from the Royal Dental Hospital of Melbourne and oral surgeons and general practitioners in private practice. Any attached soft tissues was removed and the teeth washed in distilled deionized water (DDW). All teeth in this study were sterilised by storage in a 10% (v/v) neutral buffered formalin solution for at least two weeks at room temperature. After storage in formalin the teeth were thoroughly washed in DDW and stored in DDW until required. Sound relatively planar buccal and lingual surfaces of sterilised enamel with minimal cracking, staining and fluorosis (as viewed under a dissecting microscope) were selected and thoroughly rinsed with DDW again. The outer enamel surface including superficial cracks was removed then polished wet to a mirror finish using Soflex™ (3M) polishing discs on a slow speed contra-angle dental handpiece. Each polished surface was then sawn from the tooth as an approximately 8×4 mm slab, using a water-cooled diamond blade saw and the whole slab covered with acid-resistant nail varnish except for two (occlusal and gingival) mesiodistal windows (approximately 1×7 mm) separated from each other by about 1 mm. Lesions were created in the enamel windows by mounting each slab onto the end of a 3-4 cm stick of yellow dental sticky wax and immersing in 40 mL of unagitated demineralisation buffer, consisting of 80 mL/L Noverite K-702 (polycacrylate, Lubrizol Corporation, Wickliffe, Ohio; White, 1987), 500 mg/L hydroxyapatite (Bio-Gel® HTP, Bio Rad Laboratories, Richmond CL), and 0.1 mol/L lactic acid (Ajax Chemicals, Auburn NSW) pH 4.8, for four days at 37° C. A change of solution was made after two days at which time the slabs were removed from the solution, rinsed thrice with DDW, blotted dry and placed into fresh demineralisation buffer. The slabs were similarly rinsed and dried after four days of demineralisation. This demineralisation procedure produces consistent subsurface lesions 80 to 110 µm deep with intact surface layers, as evaluated by microradiography of sections of the artificial lesions. After demineralisation, each enamel slab was sawn through the midline of each window into two 4×4 mm slabs and the cut surface of each slab covered with nail varnish. One half of each slab was retained as the demineralisation control (control half-slab) and stored in a labeled 0.5 mL microcentrifuge tube together with a drop of DDW, thereby creating a humidified environment. The other half of the enamel slab was inset into the intraoral appliance using dental wax for the remineralization protocol (test half-slab). Care was taken not to cover the artificial lesions with wax. At the end of an in situ treatment period the enamel half-slabs were removed and replaced with new pre-sterilised enamel half-slabs for the beginning of a new test period. After each treatment period each test half-slab was paired with its control half-slab and embedded, sectioned and analysed to determine mineral changes.

Each pair of enamel half-slabs (remineralization half-slab paired with its demineralisation control half-slab had the nail varnish carefully removed and was rinsed thoroughly with distilled deionised water (DDW). The pair of enamel half-slabs (test remineralization half-slab paired with its demineralisation control half-slab) was placed onto their cut sides into a small plastic vial with the lesion windows parallel and transparent cold curing methacrylate resin (Paladur, Heraeus Kulzer, Germany) poured over the half-slabs and allowed to set at room temperature. In order to identify the test and control half-slabs, a permanent identifying mark was drawn on the side of the methacrylate block next to the test enamel half-slab. Sections 200-300 µm thick were cut from the embedded half-slabs perpendicular to the lesion surface through the midline of both half-lesions using an internal annulus saw microtome (Leitz 1600, Ernst Leitz Wetzlar, Germany). The sections were then lapped down to 80±5 µm using a RotoPol¬21/RotoForce4 lapping instrument (Struers, Denmark) with 1200 grit lapping paper. The lapped sections were removed from the lapping instrument and rinsed in DDW, blotted dry and stored on soft tissue between glass slides. Each section, which contains the remineralized half-lesion and the paired demineralised control half lesion from the same enamel slab, were radiographed along with an aluminium stepwedge of 10×37.5 µm thick increments using Microchrome High Resolution glass plates (3"×3" x 0.06"; Microchrome, USA) and nickel filtered copper K$\alpha$ radiation at 20 kV and 30 mA for 8 minutes using an XMR microradiography system (Diffraction Technologies Pty Ltd) with a PANalytical fine focus glass XRD tube with a copper target (PW2213/20)) powered by a DF3 generator (Spellman High Voltage Electronics Corporation). Each glass plate was developed in Microchrome Developer D5 (1:4 dilution, Microchrome, USA) for five minutes, placed into glacial acetic acid stop bath for 30 seconds and fixed in Microchrome Developer F4 (1:4 dilution, Microchrome, USA) for five minutes. The temperature of all the photochemicals was maintained at 20° C.

Radiographic images of the lesions were viewed via transmitted light through a Dialux 20 microscope (Ernst Leitz Wetzlar, Germany). The images were acquired by a digital camera (Insight™) under the control of imaging software (Image Pro Plus version 7) running on a PC (Pentium III). Images of the lesions and the neighbouring areas of sound enamel were scanned using the program's line luminance function that gives readings in gray values between 0 and 256. An area free of artifacts or cracks was selected for analysis. Each scan comprised 200 readings taken from the tooth surface to sound enamel. The stepwedge image on each slide was scanned and the averaged step gray value readings plotted against aluminium thickness. The readings of the tooth section images were within the linear portion of the stepwedge curve and linear regression was used to convert the gray value data into values of equivalent thicknesses of aluminium. The section thicknesses were measured and the % mineral data computed using the equation of Angmar et al. (1963) and the linear absorption coefficients of aluminium, organic matter plus water and apatitic mineral (131.5, 11.3, and 260.5 respectively). The image of the median strip between the two lesions was scanned six times and averaged to give a control sound-enamel densitometric profile. The lesion images (remineralization windows and demineralisation control windows) to the gingival and occlusal side of the median strip were similarly scanned, as close as possible to the median strip but avoiding any irregularities commonly found at the lesion edges, and the % mineral profiles computed.

Example 8

In this example, a number of formulations are provided to exemplify the ways in which complexes of the invention may be formulated for different purpose compositions as described more generally above. These are only examples of the type of formulations that may be provided using various embodiments of the invention.

Toothpaste Formulations Containing Stannous-Associated Stabilized ACP or ACFP

Formulation 1

| Ingredient | A (% w/v) | B (% w/v) | C (% w/v) |
|---|---|---|---|
| Sorbitol | 53.0 | 53.0 | 53.0 |
| Silica (Zeodent 119) | 20.0 | 20.0 | 20.0 |
| Purified Water | balance | balance | balance |
| Sodium lauryl sulphate | 4.0 | 4.0 | 4.0 |
| stannous-associated stabilized ACP or ACFP | 1.2 | 1.2 | 2.0 |
| Sodium monofluorophosphate | 0.3 | — | — |
| Flavour | 1.0 | 1.0 | 1.0 |
| Sodium carboxymethyl cellulose | 0.75 | 0.75 | 0.75 |
| Titanium dioxide | 0.525 | 0.525 | 0.525 |
| Xanthan gum | 0.475 | 0.475 | 0.475 |
| Sodium saccharin | 0.350 | 0.350 | 0.350 |
| pH adjusted to 7.0 with phosphoric acid | | | |

Formulation 2

| Ingredient | % w/v | % w/v | % w/v |
|---|---|---|---|
| Sorbitol | 22.0 | 22.0 | 22.0 |
| Irish Moss | 1.0 | 1.0 | 1.0 |
| Gantrez | 19.0 | 19.0 | 19.0 |
| Purified water | balance | balance | balance |
| Sodium monofluorophosphate | — | — | 0.76 |
| Sodium saccharin | 0.3 | 0.3 | 0.3 |
| Pyrophosphate | 2.0 | 2.0 | 2.0 |
| Hydrated alumina | 47.0 | 47.0 | 47.0 |
| Flavour | 0.95 | 0.95 | 0.95 |
| stannous-associated stabilized ACP or ACFP | 1.0 | 2.0 | 2.0 |
| Sodium lauryl sulphate | 2.0 | 2.0 | 2.0 |
| pH adjusted to 5-7 with NaOH | | | |

Formulation 3

| Ingredient | % w/v |
|---|---|
| Dicalcium phosphate dihydrate | 45.0 |
| Sorbitol | 10.0 |
| Glycerol | 10.0 |
| Sodium carboxymethyl cellulose | 1.0 |
| Sodium lauryl sulphate | 1.5 |
| Sodium lauryl sarconisate | 0.5 |
| Flavour | 1.0 |
| Sodium saccharine | 0.1 |
| Sodium monofluorophosphate | 0.3 |
| Chlorhexidine gluconate | 0.01 |
| Dextranase | 0.01 |
| stannous-associated stabilized ACP or ACFP | 5.0 |
| Purified water | balance |
| pH adjusted to 5-7 with phosphoric acid | |

Formulation 4

| Ingredient | % w/v |
|---|---|
| Sorbitol | 22.0 |
| Irish moss | 1.0 |
| Gantrez | 19.0 |
| Purified water | balance |
| Sodium saccharin | 0.3 |
| Pyrophosphate | 2.0 |
| Hydrated alumina | 43.0 |
| Sodium monofluorophosphate | 0.3 |
| Flavour | 0.95 |
| stannous-associated stabilized ACP or ACFP | 5.0 |
| Sodium lauryl sulphate | 2.0 |
| pH adjusted to 5.5 with NaOH | |

Formulation 5

| Ingredient | % w/v |
|---|---|
| Dicalcium phosphate dihydrate | 45.0 |
| Sorbitol | 10.0 |
| Glycerol | 10.0 |
| Sodium carboxymethyl cellulose | 1.0 |
| Sodium lauryl sulphate | 1.5 |
| Sodium lauryl sarconisate | 0.5 |
| Flavour | 1.0 |
| Sodium saccharine | 0.1 |
| Chlorhexidine gluconate | 0.01 |
| Dextranase | 0.01 |
| Sodium monofluorophosphate | 0.3 |
| stannous-associated stabilized ACP or ACFP | 5.0 |
| Purified water | balance |
| pH adjusted to 5.5 with phosphoric acid | |

Formulation 6

| Ingredient | 1 (% w/v) | 2 (% w/v) |
|---|---|---|
| Sorbitol | 53.0 | 53.0 |
| Silica (Zeodent 119) | 20.0 | 20.0 |
| Purified water | balance | balance |
| Sodium lauryl sulphate | 4.0 | 4.0 |
| stannous-associated stabilized ACP or ACFP | 5.0 | 5.0 |
| Sodium monofluorophosphate | — | 0.3 |
| Sodium dihydrogen phosphate | 1.45 | 1.45 |
| Flavour | 1.0 | 1.0 |
| Sodium carboxymethyl cellulose | 0.75 | 0.75 |
| Titanium dioxide (Rutile) | 0.525 | 0.525 |
| Xanthan gum | 0.475 | 0.475 |
| Sodium saccharin | 0.350 | 0.350 |
| Sodium fluoride | 0.243 | — |
| pH adjusted to 5-7 with phosphoric acid/NaOH | | |

Formulation 7

| Ingredient | 1 (% w/v) | 2 (% w/v) |
|---|---|---|
| Sorbitol (70% solution) | 31.0 | 31.0 |
| Purified water | balance | balance |
| Silica | 17.0 | 17.0 |
| Glycerol | 8.0 | 8.0 |
| Sodium lauryl sulphate | 4.0 | 4.0 |
| Polyethylene glycol 300 | 1.0 | 1.0 |
| Sodium fluoride | 0.243 | — |
| Titanium dioxide (Rutile) | 0.525 | 0.525 |
| Xanthan gum | 0.475 | 0.475 |
| Sodium carboxymethyl cellulose | 0.5 | 0.5 |
| Sodium saccharine | 0.286 | 0.286 |
| Sodium acid pyrophosphate | 2.4 | 2.4 |
| Tetra sodium pyrophosphate | 2.2 | 2.2 |
| Flavour | 1.0 | 1.0 |
| stannous-associated stabilized ACP or ACFP | 5.0 | 5.0 |
| Sodium monofluorophosphate | — | 0.3 |
| pH adjusted to 5-7 with phosphoric acid/NaOH | | |

It will be understood that the invention disclosed and defined in this specification extends to all alternative combinations of two or more of the individual features mentioned or evident from the text or drawings. All of these different combinations constitute various alternative aspects of the invention.

REFERENCES

Aoba T, Fejerskov 0 (2002). Dental fluorosis: chemistry and biology. Crit Rev Oral Biol Med 13:155-70.

Den Besten P K, Thariani H (1992). Biological mechanisms of fluorosis and level and timing of systemic exposure to fluoride with respect to fluorosis. J Dent Res 71:1238-43.

Fejerskov O, Manji F, Baelum V (1990). The nature and mechanisms of dental fluorosis in man. J Dent Res 69 Spec No:692-700; discussion 721.

Fejerskov O, Yanagisawa T, Tohda H, Larsen M J, Josephsen K, Mosha H J (1991). Posteruptive changes in human dental fluorosis—a histological and ultrastructural study. Proc Finn Dent Soc 87:607-19.

Giambro N J, Prostak K, Den Besten P K (1995). Characterization of fluorosed human enamel by color reflectance, ultrastructure, and elemental composition. Caries Res 29:251-7.

Reynolds E C (1998). Anticariogenic complexes of amorphous calcium phosphate stabilized by casein phosphopeptides: a review. Spec Care Dentist 18:8-16.

Reynolds E C, Cai F, Shen P, Walker G D (2003). Retention in plaque and remineralization of enamel lesions by various forms of calcium in a mouthrinse or sugar-free chewing gum. J Dent Res 82:206-11.

Shen P, Cai F, Nowicki A, Vincent J, Reynolds E C (2001). Remineralization of enamel subsurface lesions by sugar-free chewing gum containing casein phosphopeptide-amorphous calcium phosphate. J Dent Res 80:2066-70.

The invention claimed is:

1. A stannous-associated phosphopeptide-stabilized amorphous calcium phosphate (ACP) and/or amorphous calcium fluoride phosphate (ACFP) complex having a stannous ion content of at least 1 mole of stannous per mole of phosphopeptide.

2. A stannous-associated phosphopeptide-stabilized amorphous calcium phosphate (ACP) and/or amorphous calcium fluoride phosphate (ACFP) complex according to claim 1, wherein the complex has a stannous ion content of at least 5 moles of stannous per mole of phosphopeptide.

3. A stannous-associated phosphopeptide-stabilized amorphous calcium phosphate (ACP) and/or amorphous calcium fluoride phosphate (ACFP) complex according to claim 1, wherein the complex has a stannous ion content of about 7 moles of stannous per mole of phosphopeptide.

4. A stannous-associated phosphopeptide-stabilized amorphous calcium phosphate (ACP) and/or amorphous calcium fluoride phosphate (ACFP) complex according to claim 1, wherein the stannous is provided by a compound selected from the group consisting of stannous fluoride, stannous chloride, potassium stannous fluoride, sodium stannous fluorozirconate, stannous chloride fluoride, stannous acetate, sodium stannous fluoride, stannous hexafluorozirconate, stannous sulfate, stannous tartrate, stannous gluconate, and disodium monostannous citrate.

5. A stannous-associated phosphopeptide-stabilized amorphous calcium phosphate (ACP) and/or amorphous calcium fluoride phosphate (ACFP) complex according to claim 4, wherein the compound is stannous fluoride.

6. A method of producing a stannous-associated phosphopeptide-stabilized amorphous calcium phosphate (ACP) or stannous-associated phosphopeptide-stabilized amorphous calcium fluoride phosphate (ACFP) complex according to claim 1, comprising admixing CPP-ACP or CPP-ACFP, respectively, and a stannous compound in an aqueous solution, while maintaining the pH at about 6.5 or below, wherein the complex has a stannous ion content of at least 1 mole of stannous per mole of phosphopeptide.

7. An oral care formulation comprising a stannous-associated phosphopeptide-stabilized amorphous calcium phosphate (ACP) and/or amorphous calcium fluoride phosphate (ACFP) complex according to claim 1.

8. An oral care formulation according to claim 7, wherein the composition is in the form applicable to the mouth selected from the group consisting of dentifrice including toothpaste, toothpowder and liquid dentifrice, mouthwash, mouthrinse, mouth spray, varnish, dental cement, troche, chewing gum, dental paste, gingival massage cream, gargle tablet, dairy product and other foodstuffs.

9. An oral care formulation according to claim 8, formulated as a dentifrice.

10. An oral formulation according to claim 9, wherein the dentifrice is a toothpaste.

11. A method of mineralizing a dental surface or subsurface, comprising contacting the dental surface or subsurface with a stannous-associated phosphopeptide-stabilized ACP or ACFP according to claim 1.

12. A method according to claim 11, wherein the dental surface is a lesion in the enamel caused by caries, dental erosion or fluorosis.

13. A method according to claim 11, wherein the dental surface is exposed dentine causing dentinal hypersensitivity.

14. A method of forming a protective layer bonded to the surface of the tooth, wherein the layer comprises calcium and phosphate, the method comprising contacting the dental surface or subsurface with a stannous-associated phosphopeptide-stabilized ACP or ACFP according to claim 1.

15. A method according to claim 14, wherein the layer has a calcium:phosphate ratio equivalent to normal apatite.

16. A method according to claim 14, wherein the layer contains peptides from casein phosphopeptides that stabilize the ACP or ACFP.

17. A method according to claim 14, wherein the layer contains carbon, oxygen, fluoride, phosphate, calcium and stannous.

18. A method according to claim 17, wherein the layer contains 20 to 30 wt % carbon, 35 to 45 wt % oxygen, 0.1 to 1 wt % fluoride, 8 to 12 wt % phosphate, 16 to 24 wt % calcium and 0.5 to 2 wt % stannous.

19. A stannous-associated phosphopeptide-stabilized amorphous calcium phosphate (ACP) and/or amorphous calcium fluoride phosphate (ACFP) complex according to claim 1, wherein the phosphopeptide is casein phosphopeptide.

20. A stannous-associated phosphopeptide-stabilized amorphous calcium phosphate (ACP) and/or amorphous calcium fluoride phosphate (ACFP) complex according to claim 1, wherein the ACP or ACFP in the complex is predominantly in a basic form.

* * * * *

UNITED STATES PATENT AND TRADEMARK OFFICE
CERTIFICATE OF CORRECTION

| | |
|---|---|
| PATENT NO. | : 10,912,722 B2 |
| APPLICATION NO. | : 15/105748 |
| DATED | : February 9, 2021 |
| INVENTOR(S) | : Reynolds |

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 102 days.

Signed and Sealed this
Twentieth Day of December, 2022

Katherine Kelly Vidal
*Director of the United States Patent and Trademark Office*